US012256999B2

(12) United States Patent
Shannon et al.

(10) Patent No.: US 12,256,999 B2
(45) Date of Patent: Mar. 25, 2025

(54) PLANNING SPINAL SURGERY USING PATIENT-SPECIFIC BIOMECHANICAL PARAMETERS

(71) Applicant: AGADA MEDICAL LTD., Kfar Vitkin (IL)

(72) Inventors: Samuel Shannon, Karmei Yosef (IL); Adi Dagan, Zichron Yaakov (IL); Jacov Blank, Ramat Hasharon (IL); Or Meir David, Herzliya (IL); Damon Eugene Mar, The Colony, TX (US); Isador Lieberman, Plano, TX (US)

(73) Assignee: AGADA MEDICAL LTD., Kfar Vitkin (IL)

( * ) Notice: Subject to any disclaimer, the term of this patent is extended or adjusted under 35 U.S.C. 154(b) by 0 days.

(21) Appl. No.: 18/224,367

(22) Filed: Jul. 20, 2023

(65) Prior Publication Data
US 2023/0360768 A1 Nov. 9, 2023

Related U.S. Application Data

(63) Continuation of application No. PCT/US2022/019299, filed on Mar. 8, 2022.
(Continued)

(51) Int. Cl.
*A61B 34/10* (2016.01)
*G16H 20/40* (2018.01)
(Continued)

(52) U.S. Cl.
CPC ............ *A61B 34/10* (2016.02); *G16H 20/40* (2018.01); *G16H 50/20* (2018.01); *G16H 50/50* (2018.01);
(Continued)

(58) Field of Classification Search
CPC ........ G16H 20/40; G16H 50/50; G16H 50/70; G16H 50/20; A61B 34/10; A61B 2034/102; A61B 2034/108
See application file for complete search history.

(56) References Cited

U.S. PATENT DOCUMENTS

| 10,902,944 B1 | 1/2021 | Casey et al. |
| 2003/0115031 A1 * | 6/2003 | Dariush ................. G16H 50/50 703/11 |

(Continued)

FOREIGN PATENT DOCUMENTS

| EP | 3223181 A1 * | 9/2017 | ............. A61B 34/10 |
| WO | 2020/079598 A1 | 4/2020 | |
| WO | 2020/121054 A2 | 6/2020 | |

OTHER PUBLICATIONS

Rasouli et al., "Artificial Intelligence and Robotics in Spine Surgery," Global Spine Journal 2021, vol. 11(4) 556-564; DOI: 10.1177/2192568220915718 journals.sagepub.com/home/gsj. (Year: 2021).*
(Continued)

*Primary Examiner* — Jonathon A. Szumny
(74) *Attorney, Agent, or Firm* — Michele V. Frank; Venable LLP

(57) ABSTRACT

Methods and systems for evaluating the biomechanical properties of a subject's spine for the purpose of optimizing a potential surgical intervention by selecting or designing surgical hardware fora spinal correction procedure. The system uses a simulated dynamic analysis configured to analyze, predict and improve the outcome of the surgical procedure by taking into account physiological, biomechanical, and anatomical factors. Machine learning algorithms use the computed distribution of forces and moments on the subject's spine, and compare the subject's results with those of patients from a reference population. By analyzing the biomechanical parameters of individuals in the reference
(Continued)

population and distinguishing those whose procedure succeeded versus those whose procedure failed, and comparing their biomechanical parameters to these of the individual under evaluation for a spinal surgery, the method is able to predict the chances for a successful surgery, recommend an optimal procedure and/or the optimal implant(s) configuration.

22 Claims, 14 Drawing Sheets

Related U.S. Application Data

(60) Provisional application No. 63/158,134, filed on Mar. 8, 2021.

(51) Int. Cl.
*G16H 30/20* (2018.01)
*G16H 50/20* (2018.01)
*G16H 50/50* (2018.01)
*G16H 50/70* (2018.01)
G16H 15/00 (2018.01)
G16H 50/30 (2018.01)

(52) U.S. Cl.
CPC ........ *G16H 50/70* (2018.01); *A61B 2034/102* (2016.02); *A61B 2034/104* (2016.02); *A61B 2034/105* (2016.02); *A61B 2034/108* (2016.02); *G16H 15/00* (2018.01); *G16H 30/20* (2018.01); *G16H 50/30* (2018.01)

(56) References Cited

U.S. PATENT DOCUMENTS

| | | | | |
|---|---|---|---|---|
| 2007/0171225 | A1* | 7/2007 | Haex | G06T 7/0012 345/473 |
| 2010/0217336 | A1* | 8/2010 | Crawford | G16H 50/50 606/86 R |
| 2010/0250571 | A1* | 9/2010 | Pierce | A61B 5/4528 600/587 |
| 2014/0006039 | A1* | 1/2014 | Khan | G06Q 10/0639 705/2 |
| 2014/0081659 | A1* | 3/2014 | Nawana | G16H 10/20 705/3 |
| 2014/0358576 | A1* | 12/2014 | Hoffman | G16Z 99/00 705/2 |
| 2015/0248613 | A1* | 9/2015 | Harris | G01N 5/04 706/46 |
| 2016/0310077 | A1 | 10/2016 | Hunter et al. | |
| 2017/0301088 | A1* | 10/2017 | Bharat | A61B 34/20 |
| 2018/0150929 | A1* | 5/2018 | Pheiffer | G06T 3/14 |
| 2018/0303552 | A1* | 10/2018 | Ryan | A61B 34/20 |
| 2018/0360544 | A1* | 12/2018 | Vanheule | A61B 34/10 |
| 2020/0163718 | A1* | 5/2020 | Austin | A61B 5/1121 |
| 2020/0185098 | A1* | 6/2020 | Stevens | G06N 5/022 |
| 2020/0275976 | A1* | 9/2020 | McKinnon | A61B 90/37 |
| 2020/0315708 | A1* | 10/2020 | Mosnier | A61B 17/7082 |
| 2021/0249137 | A1* | 8/2021 | Dil Nahlieli | G16H 70/40 |
| 2021/0307833 | A1* | 10/2021 | Farley | A61B 90/98 |
| 2021/0322100 | A1* | 10/2021 | Roche | G16H 10/60 |
| 2022/0142709 | A1* | 5/2022 | Zucker | G16H 30/40 |
| 2022/0157463 | A1* | 5/2022 | McKinnon | G16H 20/30 |
| 2022/0249168 | A1* | 8/2022 | Besier | A61B 5/7275 |
| 2022/0351828 | A1* | 11/2022 | Chaoui | G06N 20/00 |
| 2023/0310084 | A1* | 10/2023 | Zhang | G16H 50/50 606/1 |
| 2024/0138917 | A1* | 5/2024 | Lee | A61F 2/44 |

OTHER PUBLICATIONS

Jalalian et al., "Computational Biomechanical Modeling of Scoliotic Spine: Challenges and Opportunities," Spine Deformity 1 (2013) 401e411; http://dx.doi.org/10.1016/j.jspd.2013.07.009. (Year: 2013).*
Galbusera et al., "Planning the surgical correction of spinal deformities: toward the identification of the biomechanical principles by means of numerical," Front. Bioeng. Biotechnol. 3:178; doi: 10.3389/fbioe.2015.00178. (Year: 2015).*
Debnath et al., "Predictive Factors for the Outcome of Surgical Treatment of Lumbar Spondylolysis in Young Sporting Individuals," Global Spine Journal 2018, vol. 8(2) 121-128; DOI: 10.1177/2192568217713008 journals.sagepub.com/home/gsj (Year: 2018).*
International Search Report and Written Opinion mailed Aug. 15, 2022, directed to International Application No. PCT/US2022/019299; 23 pages.

* cited by examiner

PLANNING SPINAL SURGERY USING PATIENT-SPECIFIC BIOMECHANICAL PARAMETERS

CROSS REFERENCE TO RELATED APPLICATION

This application is a continuation of International Application No. PCT/US2022/019299, filed Mar. 8, 2022, which claims priority to U.S. Provisional Application No. 63/158,134, filed Mar. 8, 2021, the entire contents of each of which are hereby incorporated by reference.

FIELD OF THE INVENTION

The present invention relates to the field of surgical correction of spinal pathology, especially for use in improving the outcomes of spinal fusion or disc replacement procedures based on biomechanical analysis.

BACKGROUND OF THE INVENTION

Spinal surgery may be performed to reduce spinal deformities, alleviate lumbar instability, replace a herniated disc, repair traumatic injuries of the spine, and correct pathology of other etiologies. Success of a spinal operation may be measured using multiple criteria, including patient-reported symptom improvement and resolution of pain; radiographic evidence of spinal fusion and correction of spine posture; physician assessment; and objective evaluation by paramedical staff of functional recovery. Despite short term evidence of success in accomplishing the surgical goals of the operation, a large proportion of spinal surgeries either do not correct the underlying pathology, or do not relieve the primary symptoms that brought the patient for treatment, resulting in what is commonly referred to as failed back syndrome. In 2004, for example, the direct annual cost of spinal fusion surgery in the United States was over $16 billion, with an overall failure rate of estimated at between 10% and 45%. Failed back syndrome is characterized by incapacitating pain, which can worsen as scar tissue accumulates around and compresses the spinal nerve roots. Debilitation and inability to return to normal activity may necessitate a surgical revision, which has a risk of greater morbidity. Thus, finding solutions to improve the success rate of primary spinal fusion operations is of great importance.

SUMMARY

The present disclosure describes new exemplary systems for improving outcomes of spinal surgical correction procedures by taking into account the individual physical biomechanics of a patient's spine, at rest and in simulated motion, in addition to planning for correction of anatomical defects. Exemplary methods of the present disclosure apply machine learning to a database of past spinal surgical correction outcomes to distinguish between operations that succeeded and those that eventually failed. This retrospective analysis is based on calculation of at least some of forces, moments, stresses, strains, and pressures in each case, such that success or failure is defined based on whether functional score criteria are satisfied. In contrast to current planning methods based only on consideration of geometrical parameters, methods of the present disclosure explore and identify the root causes of pathology, taking into account the force moments and pressures on individual spinal segments as the spine moves. The surgical correction procedures could include spinal fusion or intervertebral disc replacement. The spinal biomechanics of the subject intended to undergo spinal fusion or disc replacement are evaluated in light of these retrospective data. Thus, the parameters of the spinal surgical correction can be planned to improve the biomechanical outcome and thus reduce the failure rate of the procedures.

An aspect of the present disclosure is to provide a method for predicting a success of a planned orthopedic surgical procedure, the method being implemented by a computer processor. The method includes receiving, by the computer processor, at least one correlation between one of post-operative and pre-operative biomechanical parameters and outcome of the orthopedic surgical procedure for each one of at least some members of a reference population; generating a virtual biomechanical model of a subject under evaluation for an orthopedic surgery, by a computer processor, using at least one of pre-operative imaging and anthropometric data of the subject; deriving, by the computer processor, at least one of pre-operative and post-operative biomechanical parameters from the generated virtual biomechanical model of the subject; and applying, by the computer processor, to at least one of the derived pre-operative and post-operative biomechanical parameters of the subject the at least one correlation to grade a predicted outcome of the planned orthopedic surgical procedure according to a predetermined rating. Applying to the at least one of the derived pre-operative and post-operative biomechanical parameters of the subject, the at least one correlation, enables grading a predicted outcome of the planned orthopedic surgical procedure according to the predetermined rating. The grading of the predicted outcome of the planned orthopedic surgical procedure enables a health practitioner to take an appropriate decision to implement or not implement the planned surgical procedure so as to optimize a chance of a successful orthopedic surgery and/or to lower a risk for an unsuccessful orthopedic surgery for the subject.

In an embodiment, prior to receiving, by the computer processor, the at least one correlation between the at least one of post-operative and pre-operative biomechanical parameters and the outcome of the orthopedic surgical procedure for each one of at least some members of a reference population, analyzing, by the computer processor, at least one of post-operative and pre-operative imaging and/or at least one of post-operative and pre-operative anthropometric data of a member of the reference population, the member having undergone an orthopedic surgical procedure, to derive the at least one of post-operative and pre-operative biomechanical parameters; grading, by the computer processor, an outcome of the orthopedic surgical procedure according to a predetermined rating; repeating, by the computer processor, the analyzing of the at least one of post-operative and pre-operative imaging and/or the at least one of post-operative and pre-operative anthropometric data and the grading of the outcome of the orthopedic surgical procedure on additional members of the reference population; and determining, by the computer processor, the at least one correlation between the at least one of post-operative and pre-operative biomechanical parameters and the outcome of the orthopedic surgical procedure for each one of the at least some of members of the reference population.

Another aspect of the present disclosure is to provide a method for predicting success of a spinal surgical procedure, the method being implemented by the computer processor. The method includes analyzing, by the computer processor, biomechanical parameters derived from at least one of pre-operative and post-operative anthropometric data, and/or at least one of pre-operative and post-operative imaging data from members of a reference population, each member having undergone a spinal surgical procedure; analyzing, by the computer processor, biomechanical parameters derived from at least one of pre-operative imaging data, post-operative biomechanical data, and anthropometric data of a subject under evaluation for a planned spinal surgical procedure; determining, by the computer processor, a likelihood of success by predicting at least one outcome of the planned spinal surgical procedure using the biomechanical parameters of at least some members of a reference population, the at least some members of the reference population being used to train an algorithm; and applying, by the computer processor, the trained algorithm to the biomechanical parameters derived from the at least one of pre-operative imaging data, post-operative biomechanical data, and anthropometric data of a subject under evaluation for a planned spinal surgical procedure. The applying, by the computer processor, the trained algorithm to the biomechanical parameters of the subject allows to at least one of a) predict a relative success of the spinal surgical procedure, or b) select of another planned spinal surgical procedure.

A further aspect of the present disclosure is to provide a system of planning a spinal surgical procedure on a subject. The system includes at least one computer processor configured to execute instructions stored on at least one non-transitory storage medium to cause the at least one computer processor to: apply to at least one of preoperative imaging data or anthropometric data of a subject, analysis of biomechanical properties of the spine of the subject encompassing at least a region of the spine needing a spinal surgical procedure; repeat the analysis of biomechanical properties after virtually performing the surgical procedure on the spine of the subject; after virtually performing the surgical procedure, inputting the analyzed biomechanical properties to an algorithm to predict a success rate of the spinal surgical procedure; and determine whether the predicted success rate meets predetermined criteria based on retrospective analysis of successful and unsuccessful past procedures from a database of prior spinal surgical procedures.

Another aspect of the present disclosure is to provide a system of planning a spinal instrumentation procedure. The system includes at least one computer processor configured to execute instructions stored on at least one non-transitory storage medium to cause the at least one computer processor to: perform on at least one of preoperative imaging data and anthropometric data of a subject, an analysis of biomechanical properties of the spine of the subject encompassing at least a region of the spine to be instrumented; repeat the analysis of the biomechanical properties after virtually embedding a potential artificial intervertebral disc into intervertebral space of a disc to be replaced from a preselected set of artificial intervertebral discs; perform the biomechanical properties analysis on imaging data of spines of subjects in a reference population who have previously undergone artificial intervertebral disc replacement procedures, performing the analysis on both preoperative imaging data and postoperative imaging data of the subject; associate the biomechanical property analysis with surgery success or failure categories; classify an output of performing the analysis of biomechanical properties of the spine of the subject and performing the analysis on both preoperative imaging data and postoperative imaging data of the subject into one of success or failure categories to predict success rate of a given artificial intervertebral disc replacement procedure; and determine whether predicted success rate meets predetermined criteria for the potential artificial intervertebral disc to be replaced.

Another aspect of the present disclosure is to provide a method for predicting a success of a planned spinal surgical procedure, the method being implemented by a computer processor. The method includes generating, by the computer processor, a virtual biomechanical model of a subject needing a spinal surgery using at least one of imaging data and anthropometric data; deriving, by the computer processor, at least one of pre-operative and post-operative biomechanical parameters of the subject needing the spinal surgery from the virtual biomechanical model; receiving, by the computer processor, at least one predefined correlation between (i) at least one of post-operative and pre-operative biomechanical parameters and (ii) a known outcome of a prior spinal surgical procedure for each one of a plurality of previous patients that had a spinal condition; and determining, by the computer processor, a chance for success/failure for the subject needing the spinal surgery using the at least one predefined correlation and at least one of the pre-operative and the post-operative biomechanical parameters of the subject needing the spinal surgery. Determining the chance for success/failure for the subject needing the spinal surgery enables a health practitioner to take an appropriate decision to implement or not implement a planned spinal surgical procedure so as to optimize a chance of a successful orthopedic surgery and/or to lower a risk for an unsuccessful orthopedic surgery for the subject.

In an embodiment, receiving, by the computer processor, the at least one predefined correlation between (i) at least one of post-operative and pre-operative biomechanical parameters and (ii) a known outcome of a prior spinal surgical procedure for each one of the plurality of previous patients that had a spinal condition includes: generating, by the computer processor, a virtual biomechanical model for each one of the plurality of previous patients that had a spinal condition using at least one of pre-operative imaging data and anthropometric data corresponding to each one of the plurality of previous patients; deriving, by the computer processor, pre-operative biomechanical parameters of each one of the plurality of previous patients using the virtual biomechanical model generated for each one of the plurality of previous patients; and determining, by the computer processor, using a trained machine learning algorithm, a correlation between at least one of post-operative and pre-operative biomechanical parameters and a success/failure of the spinal surgery.

In another embodiment, receiving, by the computer processor, the at least one predefined correlation between (i) at least one of post-operative and pre-operative biomechanical parameters and (ii) a known outcome of a prior spinal surgical procedure for each one of the plurality of previous patients that had a spinal condition includes: generating, by the computer processor, a virtual biomechanical model for each one of the plurality of previous patients that had a spinal condition using post-operative imaging data corresponding to each one of the plurality of previous patients; deriving, by the computer processor, post-operative biomechanical parameters of each one of the plurality of previous patients using the virtual biomechanical model generated for each one of the plurality of previous patients; and determining, by the computer processor, using a trained machine learning algorithm, a correlation between at least one of post-operative and pre-operative biomechanical parameters and a success/failure of the spinal surgery.

A method for planning an orthopedic surgical procedure, the method being implemented by a computer processor. The method includes receiving, by the computer processor, at least one target for a planned orthopedic surgical procedure, the at least one target relating to biomechanical parameters being derived from a virtual biomechanical model of one or more healthy subjects and/or one or more subjects that have undergone a successful or failed surgery and/or existing reference data for one or more of bones, ligaments and muscles comprising a spine of a plurality of previous patients that had a spinal condition; generating a virtual biomechanical model of a subject under evaluation for an orthopedic surgery, by a computer processor, using at least one of pre-operative imaging data and anthropometric data of the subject; simulating, by the computer processor, the planned orthopedic surgical procedure to predict post-operative biomechanical parameters of the subject using the generated virtual biomechanical model of the subject; and applying, by the computer processor, to the predicted post-operative biomechanical parameters of the subject the at least one target to compare a predicted outcome of the planned orthopedic surgical procedure that is based on the post-operative biomechanical parameters of the subject with the at least one target. Applying to the predicted post-operative biomechanical parameters of the subject, the at least one target, enables grading a predicted outcome of the planned orthopedic surgical procedure according to a predetermined rating. The grading of the predicted outcome of the planned orthopedic surgical procedure enables a health practitioner to take an appropriate decision to implement or not implement the planned surgical procedure so as to optimize a chance of a successful orthopedic surgery and/or to lower a risk for an unsuccessful orthopedic surgery for the subject.

Another aspect of the present disclosure is to provide a method for predicting a success of a planned spinal surgical procedure, the method being implemented by a computer processor. The method includes generating, by the computer processor, a virtual biomechanical model for each one of a plurality of previous patients that had a spinal condition using at least one of pre-operative imaging data and anthropometric data corresponding to each one of the plurality of previous patients; deriving, by the computer processor, at least one of pre-operative and post-operative biomechanical parameters of each one of the plurality of previous patients using the virtual biomechanical model generated for each one of the plurality of previous patients; and determining, by the computer processor, using a trained machine learning algorithm, a correlation between at least one of post-operative and pre-operative biomechanical parameters and a success/failure of a spinal surgical procedure for each one of the plurality of previous patients.

In an embodiment, the method further includes generating, by the computer processor, a virtual biomechanical model of a subject needing a spinal surgery using at least one of imaging data and anthropometric data; deriving, by the computer processor, at least one of pre-operative and post-operative biomechanical parameters of the subject needing the spinal surgery using the virtual biomechanical model; receiving, by the computer processor, the at least one correlation between (i) the at least one of post-operative and pre-operative biomechanical parameters and (ii) the success/failure of the spinal surgical procedure for each one of the plurality of previous patients; and determining, by the computer processor, a chance for success/failure for the subject needing the spinal surgery using the at least one correlation and at least one of the pre-operative biomechanical parameters and the post-operative biomechanical parameters of the subject needing the spinal surgery. Determining the chance for success/failure for the subject needing the spinal surgery enables a health practitioner to take an appropriate decision to implement or not implement a planned spinal surgical procedure so as to optimize a chance of a successful orthopedic surgery and/or to lower a risk for an unsuccessful orthopedic surgery for the subject.

Another aspect of the present disclosure is to provide a method for predicting a success of a planned spinal surgical procedure, the method being implemented by a computer processor. The method includes receiving, by the computer processor, reference data; generating, by the computer processor, a virtual biomechanical model of a subject under evaluation for an orthopedic surgery, by a computer processor, using at least one of pre-operative imaging data and anthropometric data of the subject; simulating, by the computer processor, the planned orthopedic surgical procedure to predict post-operative biomechanical parameters of the subject using the generated virtual biomechanical model of the subject; and applying, by the computer processor, to the predicted post-operative biomechanical parameters of the subject the reference data. Applying to the predicted post-operative biomechanical parameters of the subject, the reference data, enables grading a predicted outcome of the planned orthopedic surgical procedure according to a predetermined rating. The grading of the predicted outcome of the planned orthopedic surgical procedure enables a health practitioner to take an appropriate decision to implement or not implement the planned surgical procedure so as to optimize a chance of a successful orthopedic surgery and/or to lower a risk for an unsuccessful orthopedic surgery for the subject.

In an embodiment, the reference data includes (a) at least one target for a planned orthopedic surgical procedure, the at least one target relating to biomechanical parameters being derived from (i) a virtual biomechanical model of one or more healthy subjects, (ii) one or more subjects that have undergone a successful or failed surgery, and/or (iii) existing reference data for one or more of bones, ligaments and muscles comprising a spine of a plurality of previous patients that had a spinal condition, and/or (b) at least one correlation between at least one of post-operative and pre-operative biomechanical parameters and outcome of the orthopedic surgical procedure for each one of at least some members of a reference population.

Another aspect of the present disclosure is to provide a method for predicting a success of a planned orthopedic surgical procedure, the method being implemented by a computer processor. The method includes receiving, by the computer processor, reference data, generating, by the computer processor, a virtual biomechanical model of a subject under evaluation for an orthopedic surgery, by a computer processor, using at least one of pre-operative imaging data, post-operative imaging data and anthropometric data of the subject to generate a virtual biomechanical model of the subject under evaluation, simulating, by the computer processor, the planned orthopedic surgical procedure including incorporating a simulated implant(s) into the generated virtual biomechanical model of the subject, comparing, by the computer processor, results of the simulation with the reference data, and determining, by the computer processor, whether stresses on the implant(s), bones, ligaments and muscles are exceeding a failure point of the implant(s) based on the reference data.

In an embodiment, the reference data includes at least one of (a) reference data from one or more subjects that have undergone a successful or failed surgery, and (b) existing reference data for one or more of bones, ligaments and muscles comprising a spine of a plurality of previous patients that had a spinal condition.

In another embodiment, the reference data comprises at least one of data in a book, data in a reference document, and data from an online data source relating to one or more of (i) bones, ligaments and/or muscles of a human patient, (ii) structural features of one or more implants, (iii) material properties of one or more implants, and (iv) forces exerted on a spine of a human patient.

BRIEF DESCRIPTION OF THE DRAWINGS

The presently claimed embodiments of the invention will be understood and appreciated more fully from the following detailed description, taken in conjunction with the drawings in which:

DETAILED DESCRIPTION

Figure 1:
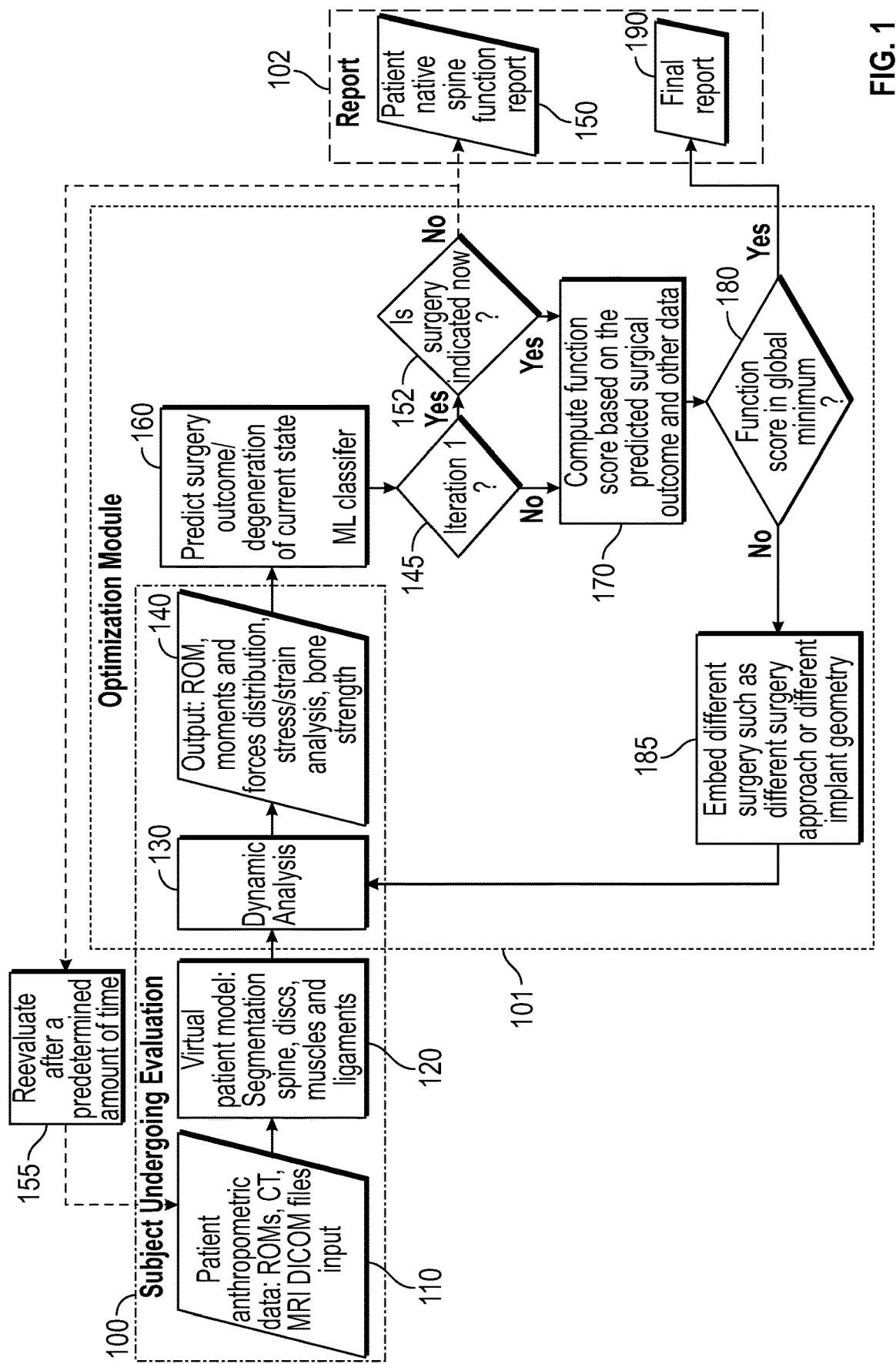
FIG. 1 shows a flow chart of steps taken in an exemplary implementation of the disclosed methods for predicting an ideal implant.

An avenue of pursuit in improving current treatment methods is the personalization of spinal surgical procedures, based on individual anatomic characteristics of the patient to be treated. These methods attempt to measure or calculate anatomical features of the patient from two- and three-dimensional preoperative imaging studies, such that the spinal alignment parameters and other anatomical aspects can be quantified. Based on these quantitative measurements, known relevant parameters can be measurably improved. Therefore, a number of current exemplary methods and systems have been developed to generate custom implants for spinal stabilization or correction. Such methods programmatically analyze a patient's preoperative imaging data to obtain shapes and dimensions of relevant anatomical features of a target region of the patient, and potential implants to rectify the anatomical defects. Patient-adapted articular repair systems have been developed using parameterized models and/or multibody simulations. Preoperative imaging may be used to assess the size, shape and condition of the relevant patient anatomy in order to customize the size and shape of an implant for a specific patient. The unprocessed electronic image data can be used to create one or more representations or "models" of the patient's anatomy, including two-dimensional or three-dimensional physical reproductions of the patient anatomy. Such models can then be used to select or design an orthopedic implant(s) appropriate for the patient's anatomy. These various proposed solutions are based on customizing the solution to the patient's anatomy.

Customization of the spinal correction procedure to the patient is relevant for preventing secondary complications. For example, after performing a spinal fusion, a potential complication of fusing vertebral segments is the subsequent development of adjacent segment degeneration. While spread of the degeneration to spinal segments adjacent to the fusion may indicate further spread of the natural degenerative process, the process may be due in part to the altered biomechanics adjacent to fused spine segments. Additionally, a percentage of patients develop instability at one or both of the rostral and caudal adjacent levels following an operation for spinal stabilization. These secondary pathologies are a result of physiological forces and spinal dynamics that may be independent of the anatomical considerations that were taken into account in planning the spinal correction procedure. These forces may change as, for example, two vertebrae are fused. Failure to account for these expected or predictable changes in force and moments may lead to secondary complications such as adjacent segment disease, resulting from stress or strain brought to play on the vertebrae above and below a fused joint.

The realization of the importance of spine dynamics has led to another category of methods intended to improve the outcome of spine operations, comprising modeling spine mechanics to take the relevant biomechanical forces into consideration in planning the spinal correction. One such suggested solution is a process using the kinematics of a spinal motion segment, determined by the material properties of the soft-tissue and anatomy. This method is based on a given range of motion and morphology of a subject's spine, and identifies relevant material parameters associated with the kinematics of a spinal motion segment. These identified parameters are then used to develop a parametric finite element model of the morphology and material properties of lumbar spinal motion segments. A limitation of these methods would appear to be that because such simulations are theoretical in nature, they rely on predictions rather than determining the actual linear and rotational forces that would come to play on the human spine post-operatively. Thus, although musculoskeletal simulation systems exist that can simulate a patient's specific spine and analyze the forces and moments that develop within it while the spine is moving, none of them is able to predict whether an intended surgical intervention, including the use of implants, will result in a successful vs. a failed outcome.

Practical application of predictions of surgery outcomes remains theoretical for several reasons. Besides lacking a means to validate the simulation measurements and their implications for the patient's spine dynamics both pre-operatively and post-operatively, the plethora of data that can be generated using multiple parameters, alone and in combination, leaves the investigator without a clear indication of the most important parameters to optimize. To date, no system is configured to provide answers to the relevant questions in optimizing the subject's biomechanical data. Additionally, the clinical relevance of results of a biomechanical study can only be determined for a given patient retrospectively, i.e., postoperatively. As it is difficult to know a priori the clinical significance and accuracy of the biomechanical parameter data provided by the simulation, such systems are not useful as diagnostic or predictive tools to help the physician decide on the most appropriate treatment for a given patient.

In summary, personalized spinal implants customizing a spinal correction procedure based on geometric considerations account for only the anatomical component of a patient's spinal alignment. Personalization based on biomechanical considerations takes the physiological component of the individual's spine dynamics into account; however, measurements or predictions of postoperative parameters are difficult to calculate or simulate preoperatively. Therefore, there exists a need for a method and system that will enable better planning and prediction of surgery outcomes, both for deformity correction surgeries and other spinal procedures. The need is for a means of optimizing and personalizing spinal parameters preoperatively to improve the results of spinal correction procedures, which overcomes at least some of the disadvantages of prior art systems and methods.

Implementations of the disclosed system and methods are configured to provide successful alternatives to prior art options of surgical planning. Methods of the present disclosure rely on data generated by the biomechanical analysis of a physiological model of specific patients, in simulated motion of pre- and post-operative states. These analyzed biomechanical data of dynamic bodies may be applied to data for a current potential patient, allowing evaluation of the need for surgical intervention, and prediction of the success/failure of planned spine surgeries, if indicated. An advantage of this method is that it provides the ability to validate or predict the expected outcome of a planned procedure on a new patient even though a patient with similar geometrical anatomy is not found in the data base. Another advantage is the ability to compare predicted biomechanical results of different existing implants and existing surgical techniques. Finally, implementations of the present methods allow determination of the configuration (geometry and motion/stiffness) of the optimal implant or set of implants.

The present disclosure describes a method and a system configured to diagnose a patient's current spinal strength, rigidity and range of motion, and to predict the likelihood of success or failure of an intended surgical intervention, based on machine learning algorithms and/or reference data applied to individual patient imaging data. The method determines biomechanical parameters during motion simulation in order to achieve the predictions. For this purpose, in an embodiment, the system is first trained on retrospective data of many patients taking into consideration forces, moments, pressures, and rigidity on top of geometrical data from a reference population with known preoperative status; surgical procedure performed, if any; and post-operative data if relevant. The data may comprise the patient's pre-operative and post-operative imaging studies, for example in DICOM format, anthropometric data, demographic data, and follow-up either without surgery, or with a surgical outcome comprising the degree of success or failure.

In an embodiment, the method is based on machine learning algorithms that are trained on post-operative and in some cases also pre-operative anthropometric, demographic, and biomechanical parameter study data from a number of patients in a reference population who suffer from specific spinal conditions. The algorithm is programmed to distinguish the successful outcomes from failures based on biomechanical properties. The algorithm is configured to search and define: a) a range of the simulated results that are associated with a successful or unsuccessful outcome, in each of the parameters measured by the simulation, and b) other algorithms that use as input the pre-operative and/or post-operative simulated biomechanical analysis results to predict the likelihood of success or failure of the intended spinal corrective procedure on the individual subject under evaluation. The biomechanical analyses may include forces, moments, pressures, strains and other biomechanical factors, as the main predictors of successful or unsuccessful procedures, in addition to geometrical or anatomical correction. The comparisons are made on a subset of the reference population that suffers from the same spinal condition or similar biomechanical abnormalities as that of the current patient.

Implementations of the method use musculoskeletal simulation systems comprising a computer representation of the human body, generally that of a specific patient. Once the representation is created by converting the patient's imaging studies and anthropometric data into a computer readable form, the computer can simulate the body in motion, using software that uses technologies such as finite element analysis and inverse dynamics. The output of the analysis comprises biomechanical data regarding the forces and moments that develop in the patient's spine through its movement. The system may be configured to analyze the biomechanical forces and other parameters that are applied to each segment of the spine, and in each of the different structures that comprises a segment, such as the vertebrae, the intervertebral discs, the facet joints, and the ligaments and muscles surrounding each segment.

To date, although a number of musculoskeletal simulation systems have been developed to simulate a patient's specific spine and analyze the forces and moments that develop within it while the spine is moving, none is able to predict whether an intended surgical intervention, including the use of implants, will result in a successful or unsuccessful outcome. Current methods of planning surgical correction of spinal pathology generally take into account anatomical aberrations, which the surgeon attempts to rectify by implanting hardware. The purpose of the implanted hardware is to stabilize the spine and/or to bring measurable geometrical spinal parameters into physiological alignment, with goals that may include reducing pain, restoring function, and/or preserving range of motion. The achievement of these goals is variable and depends on many factors, some of which are patient-specific and some of which depend on the surgeon's choice of instrumentation and surgical technique. Although measurements of geometrical spinal parameters such as lumbar lordosis (LL), pelvic tilt (PT), sacral slope (SS) and sagittal vertebral axis (SVA) are useful, they do not take into account physiological changes during motion. The final long-term outcome in terms of the patient's quality of life and function are dependent not only on correction of anatomically-dependent spinal parameters, but also on biomechanical factors. Thus, in some cases, anatomical adjustment of the spinal parameters does not result in the expected improvements in patient-reported relief of pain and disability. Relevant physiological or biomechanical factors comprise the forces, moments, pressures, and stresses and strains that act on the subject's spine, as well as physiological factors such as bone and ligament strength. The spinal range of motion in various positions, such as flexion and extension, lateral bending and axial rotation, are important factors in determining the success or failure of an operation.

An advantage of the present disclosure is that studying the biomechanics of the patient's spine by such simulation may be performed with respect to the patient's situation both before and after the surgical intervention, which may include the use of implants. Implementations of the disclosed methods are enabled to simulate the surgical intervention, e.g., the cutting of bones and ligaments in the model, and to create a computer representation of the implant(s) shape and associated material properties after being embedded in the digital model of the patient's spine at rest and in motion. The methods may also provide information on the redistribution of forces and moments to adjacent spinal levels after a simulated spinal procedure. The method output may include predictions of the patient's future biomechanical parameters without surgery, or after an intended surgical intervention. The method is able to determine whether certain biomechanical parameter results are associated with successful surgeries while others are associated with failed surgeries.

Incorporating postoperative biomechanical considerations into planning a spinal corrective procedure could significantly improve outcomes of these operations. However, currently it is difficult to preoperatively measure or simulate in a given individual the effect of a surgical procedure on postoperative function. Implementations of the present disclosure are designed to perform preoperative analysis on a subject's biomechanical and physiological spinal function. This analysis comprises segmentation analysis of the subject's preoperative imaging studies, providing information on bony and soft tissue elements of the spine. The output of the segmentation analysis is used as input to the dynamic solver an optimization module that comprises additional dynamic analysis of anticipated range of motion, force and moment distribution, stress and strain analysis on hard and soft tissue and bone strength on the subject under evaluation. Soft tissues may comprise ligaments, muscles, tendons, and other connective tissue elements. These analyses are accomplished using methods such as inverse dynamics and finite element analysis. In turn, the output from this analysis is input to a machine learning algorithm and/or compared to reference data for predicting the outcome of a given spinal correction procedure. The algorithm uses clustering or classification techniques to divide outcomes of spinal correction procedures performed on individuals in a reference population into two or more groups, based on success or failure of the operation. The system analyzes the biomechanical factors of the individuals in the reference population based on both pre- and post-operative imaging studies, using the same analytical methods as used for the subject under analysis. Thus, the system is able to match the biomechanical characteristics of the subject to previous patients, and select the surgical procedure most likely to produce a successful outcome. In selecting the best spinal correction procedure, the system takes into account not only the specific procedure, such as, for example, artificial intervertebral disc replacement vs. spinal fusion, but also the surgical approach and type of surgical instrumentation to implant, and the strengths and forces that will be generated by the implants on the subject's spine at rest and in motion.

A musculoskeletal simulation system is a computer representation of the human body. The representation can be of a generic human being or that of a specific patient. In the case of a specific patient, the simulation system is derived from the patient's imaging studies such as CT, MRI, and X-rays, and anthropometric data such as BMI, weight, height, and other quantitative measurements of the individual. These measurements are converted into a computer readable form, such as CAD, enabling computer simulation of the body in motion, using software that employs technologies such as finite element analysis (Abaqus) or inverse dynamics (Anybody Tech). The output of the analysis provides data on biomechanical forces and other parameters, e.g., the forces and moments that develop in the patient's spine during movement, at each segmental level of the spine. For each spinal segment, each of the structures that comprises the segment, such as the vertebrae, the intervertebral discs, the facet joints, and the ligaments surrounding them are analyzed. The biomechanical parameter study of the patient's spine by such simulation may be performed with respect to the patient's situation before any surgical intervention. The patient's spine biomechanics may also be simulated after a virtual surgical intervention including the use of implants. The surgical intervention may be simulated by virtually cutting bones and ligaments in the digital model of the patient's spine, creating a computer representation of the shape and material properties of surgical hardware to be implanted, and virtually embedding the hardware in the patient's model. The biomechanical evaluation of the patient's spine pre- and post-operative states provides a powerful tool in assessing the impact of the symptomatic state on spine biomechanics, and predicted effectiveness of the treatment outcome. The system provides the ability to predict the progression of the patient's pathology over time, either or both without surgery or with an intended surgical intervention.

The ability to use simulation systems to predict progression of disease or the effect of surgical treatment has been hampered because of the difficulty in validating measurements. For example, in an exemplary implementation, a full study of biophysical parameters of a subject's spine evaluates ten indices that relate to the forces impinging on each of over 30 spinal segments during motion. Thus, the readout generates over 300 quantitative readings, whose values are specific to the subject under evaluation. The challenge is then to determine which levels and which parameters at each level have the highest clinical relevance for the patient's condition and planned surgical intervention. An advantage of the current methods and systems is the ability to determine and validate the clinical significance of specific biomechanical parameters, for use as diagnostic and predictive tools to help the physician decide on the most appropriate treatment for the patient.

Following is the description of a method and a system that uses machine learning on the data provided by running a parametric study on a patient's simulation in order to evaluate the patient current state and predict the likelihood of a success or failure of an intended surgical intervention, according to embodiments of the present disclosure. In order to do so, the system is first trained on retrospective data of many such patients for which the pre-operative, operative, and post-operative data are available. The input data to the algorithm include the patient's DICOM (pre and post-operative), anthropometric data, demographic data and post-operative or non-operative outcomes. The outputs comprise both the anatomical/geometrical shape of spinal elements as well the physiological/biomechanical data such as forces, moments, pressures, and strengths of each hard and soft tissue of each spinal segment. The outcomes may be classified in several ways: binarily as success/failure; as a multiclass scale (success, lack of success, and degree of success); or on a continuous regression scale.

The machine learning algorithm runs on the pre- and post-operative parametric study data (and the anthropometric and demographic one) from many patients which suffered from a certain spinal condition, knowing which ones ended with a successful result and which with a failed one it searches and comes up with: 1) the range of the simulated results that are associated with a successful/failed outcome, in each of the parameters measured by the simulation, and 2) an algorithm that uses as an input the pre-operative and/or postoperative simulated biomechanical analysis results to predict the likelihood of a success/failure of the intended surgery.

A number of available pre-operative spinal surgery planning software programs rely on static geometric analyses of the subject's pre-operative posture as reflected in his imaging studies to predict the post-operative outcome based on anatomical simulations, the intended positioning of implants, and their effect on patient posture. Such programs applicable to the analysis of a geometrical static position are useful in surgical correction of spinal deformities. While good theoretical corrections may be predicted, a failure rate of up to 50% or more may occur in complex spine surgeries. Whereas actual post-operative anatomical findings may align with the predicted outcome, in a significant portion of these cases, the operation unexpectedly fails to relieve the patient's signs and symptoms.

The present invention describes the use of a biomechanical study of a patient-specific anatomic, biomechanical and physiologic system, comprising a virtual model that includes the patient's bones ligaments and muscles to analyze the patient situation pre op and predict post-operative outcomes. Instead of measuring geometrical indices and using them to reach an optimal outcome based on literature data we use forces and moments that are generated through the spine movement to reach the optimal outcome. In contrast to software programs that rely on static geometrical analysis of a moving object, e.g. the spine, implementations of the present invention use analysis of biomechanical parameters, more physically and physiologically relevant to analysis of moving body parts, which might be the root cause for a successful or failed procedure.

For example, according to one embodiment, the disclosed method can include (a) creating a musculoskeletal/biomechanical model of the patient from DICOM and/or anthropometric data, (b) using the model to (i) derive biomechanical parameters of the patient's pre-op situation, (ii) simulate an intended surgery with the potential use of implants and/or (iii) derive biomechanical parameters of the simulated post-surgery situation, (c) using a predefined correlation between one of the pre- and post-operation biomechanical parameters and a successful/failed surgery to determine the chance for success/failure for this specific patient. In order to determine the predefined correlation, an ML algorithm is trained on retrospective data of patients that had a spinal condition, went through a surgery, and to which the surgery outcome is known and the pre-op and post-op DICOM for this patient is known. For these previous patients, step (a) above of creating a musculoskeletal/biomechanical model is done for both the pre-op and post-op situation for each patient, biomechanical data is derived for both the pre-op and post-op situations, and ML algorithm is used to try and find a correlation between at least one of the pre-op and the post-op biomechanical parameters and the success/failure. This correlation is then used in step (c) discussed above. According to an embodiment, the training of the ML algorithm, as discussed above, uses a musculoskeletal model that is created based on the post-op situation of the previous patient using the patient's post-op DICOM, as opposed to a simulated musculoskeletal model that is created for the post-op situation when evaluating a new patient (see, e.g., steps (a) to (c) above).

Implementations of the current disclosed methods may be used in at least the following ways:
1) the data derived from a virtual patient-specific digital model may be used to analyze patient current biomechanical spine function and predict future post-operative biomechanical function;
2) the biomechanical parameter study data derived from a patient-specific digital model may be used to define the best surgical approach and the best configuration of implants from those currently available;
3) biomechanical parameter study data derived from the patient-specific digital model may be used to define the optimal geometrical and biomechanical attributes of an implant or set of implants; an implant will be tailored according to the parametric studies results, currently there aren't any such implants in the market;
4) running biomechanical parameter studies on data of numerous successfully and unsuccessfully operated patients, and using a machine learning algorithm defined in the Description to determine the parameters important to reach a successful post-operative outcome;
5) using machine learning algorithms on biomechanical parameter studies on:
a) post-operative data of successfully operated patients to determine the range of values of the relevant and important parameters required to reach a successful outcome, and those associated with clearly unsuccessful outcomes;
b) pre- and post-operative data of successfully and unsuccessfully operated patients to determine the parameters, and the range of values for each parameter, important to reach a successful outcome, and those associated with failure.
c) defining an equation that takes into account the important parameters and ranges of values for each parameter, and determining the relative weight of each important parameter in defining the biomechanical factors that contribute to a successful outcome in a particular patient having a specific disease.

A method for achieving the above may include the following steps:
a) building a virtual anatomical and physiological model of the patient;
b) running a biomechanical parameter study on the model in virtual motion;
c) employing correction maneuvers on the model, e.g. changing structure of biological tissues and inserting implants, and evaluating their influence on the biomechanical parameters; and
d) employing an optimization algorithm on the model to define the biomechanical attributes such as geometrical shape and stiffness, of an ideal surgical plan and at least one ideal implant.

The methods may be implemented by the system to predict the surgical intervention most likely to achieve spinal correction; alternately, the surgeon may select various surgical interventions to be tested by the system, selecting from the options the intervention predicted to produce the best post-operative outcome.

In some implementations of the disclosed system and methods, the method evaluates a number of possible spinal implants to determine the one most likely to give long term postoperative success. For example, in the case of an artificial intervertebral disc replacement, a number of potential implants having different biomechanical properties may be evaluated using the disclosed algorithms. Choosing the one with the physiological characteristics most compatible and suitable for the subject will increase the chances of a successful outcome.

Definitions of terms used throughout the disclosure are provided herein as follows:

Biomechanical parameters, as defined in this specification, are parameters relating to the physiology and biophysics of the spine, comprising the forces, moments, torques, stresses, and resulting strain on a subject's spine, or on a spine-implant assembly. Bone strength and density, and anthropometric data may also be considered biomechanical parameters.

Classifier, for the purposes of this disclosure, is a hypothesis or discrete-valued function that is used to assign categorical class labels to particular data points using a machine learning algorithm.

Cluster analysis, or clustering, is an unsupervised machine learning task involving automatically discovering natural grouping in data, performing the task of grouping a set of objects in such a way that objects in the same group are more similar to each other than to those in other groups. Clustering algorithms interpret the input data and find natural groups or clusters in feature space.

Convolutional neural network (CNN) is a deep learning neural network designed for processing structured arrays of data such as images.

Digital imaging and communications in medicine (DICOM) is the standard for the communication and management of medical imaging information and related data, most commonly used for storing and transmitting medical images enabling the integration of medical imaging devices.

Finite element analysis (FEA) is a process of simulating the behavior of a part or assembly under given conditions so that it can be assessed using the finite element method, the most widely used method for solving problems of engineering and mathematical models.

Inverse dynamics analysis is typically based on measurements of the kinematics of the body segments, often complemented with measurement of selected external forces (e.g. the ground reaction force).

Musculoskeletal model A computational model that encompasses a skeleton consisting in rigid body segments (bones) connected by joints. The skeleton may have several constraints (e.g.: maximum joint angles). Muscles spanning from joints are connected to bones via tendons. Muscles are able to generate forces and movement.

Reference is now made to FIG. 1, which illustrates schematically an overview of the main steps involved in an exemplary implementation of the present disclosure to plan a preferred implant configuration to improve the postoperative outcome of a planned spinal correction procedure. Module 100 represents parameters and results of a subject to be evaluated for a spinal correction procedure such as spinal fusion or artificial disc replacement, which comprise the input for the disclosed methods. Optimization module 101 represents the optimization module used for planning and predicting the geometry and biomechanics of an ideal implant or set of implants to correct the biomechanics of the subject under evaluation. Box 102 (Report) represents the output of the analysis, either of the subject's preoperative condition 150, detailing the anatomical and physiological pathology, or the predicted parameters of the ideal parameters of an implant and planned instrumentation after performance of a spinal correction procedure using a specific implant or set of implants.

Reviewing each of these main steps in detail, the input to the anthropometric data 110 comprises subject demographic data such as age, gender, and smoking status; anthropometric data such as body mass index, height, weight, spinal range of motion, and bone density; and imaging data such as x-ray, CT, and MRI files in DICOM (digital imaging and communications in medicine) format. The DICOM standard specifies a non-proprietary data interchange protocol, digital image format, and file structure for biomedical images and image-related information. From these inputs, a virtual subject model 120 is built, showing a virtual segmented model of the patient's spinal anatomy comprising bony and soft tissue elements. The derived information in this model has data comprising segmentation of the spine: vertebrae, intervertebral discs, muscles, and ligaments. These data are used as input to the optimization module 101. Dynamic analysis 130 is performed on the data obtained from step 120. The dynamic analysis may comprise various biomechanical studies of forces and moments, stresses and strains, such as finite element analysis of the spinal structures such as that available from Abaqus Unified FEA; Velizy-Villacoublay, France, and ergonomic optimization using an available software system such as that available from AnyBody Technology; Aalborg, Denmark. The output of the dynamic analysis 140 comprises range of motion (ROM), distribution of moments and forces, stress and strain analysis, and bone strength. The output of 140, proceeds to step (machine learning algorithm) 160 of the optimization module 101 in order to plan a spinal correction procedure.

The machine learning algorithm 160 predicts the outcome of surgery using the subject's native spine functions. The prediction is based on comparison of the current subject's output to known sets of success or failure outputs for similar operations on patients with similar biomechanical properties. Determining the difference between success or failure outputs is based on additional novel machine learning algorithms that have been independently trained on retrospective data. These outputs are then used for predictive classification of the subject under evaluation, as further explained and described in FIGS. 5A to 8. Based on the machine learning algorithm 160, a report 150 of the subject's native spine function is generated. In step 152, an evaluation is made as to whether the subject's pathology is severe enough to warrant immediate surgical correction. This decision may be made by the surgeon, or by predetermined criteria input into the system. If not, the analysis could be repeated over time (step 145, iteration) by returning to module 100 and repeating the evaluation as needed until a decision is made to operate and which operation to perform. Such repeated evaluations over time allow a quantitative view of the clinical time course of the patient under evaluation and allow the system to predict when surgical repair is likely to be needed. The report provides information on the pathological parameters of the spine that necessitate an evaluation for surgical correction.

The prediction algorithm (e.g., machine learning algorithm) 160 generates several predictive metrics that provide the surgeon with a quantitative ranking of various possible operations and implants. In step 170, the system applies steps 130 and 140 to determine the geometrical and biomechanical parameters of an ideal set of implants for the subject. Using the biomechanical parameters (e.g., moments, force distribution, stress, strain analysis, bone strength, etc.) from step 140 as applied to the current patient's spine, the algorithm at 170 will output function scores 180 that reflect the improvement expected from a given implant or set of implants for a selected surgical procedure. The possibility exists that one planned operation will give a higher percent chance of success, e.g., spinal fusion, but another operation will have a slightly lower percent chance of long-term success, e.g., AIDR, but allow greater range of motion. The function score may be configured to provide percent success in a binary manner, i.e., success/failure only, or it may also consider other factors. In some cases, the function scores will have a cutoff value or range of values for each biomechanical parameter associated with either a successful or a failed outcome, such that the system uses a weighted sum of parameters to define what is expected to be a successful outcome of the procedure. In some exemplary implementations of the disclosed methods, the prediction provides an optimal anatomical and physiological solution, and the system then outputs instructions for three-dimensional printing or manufacture of an implant that matches the desired biomechanical and geometric parameters. In step 185, optimization of parameters may be based on at least one of the surgical approaches, the number of spinal segments to be operated, and the type of implant to be inserted at each intervertebral level, comprising implant stiffness, implant height and angle of the implant.

Figure 2:
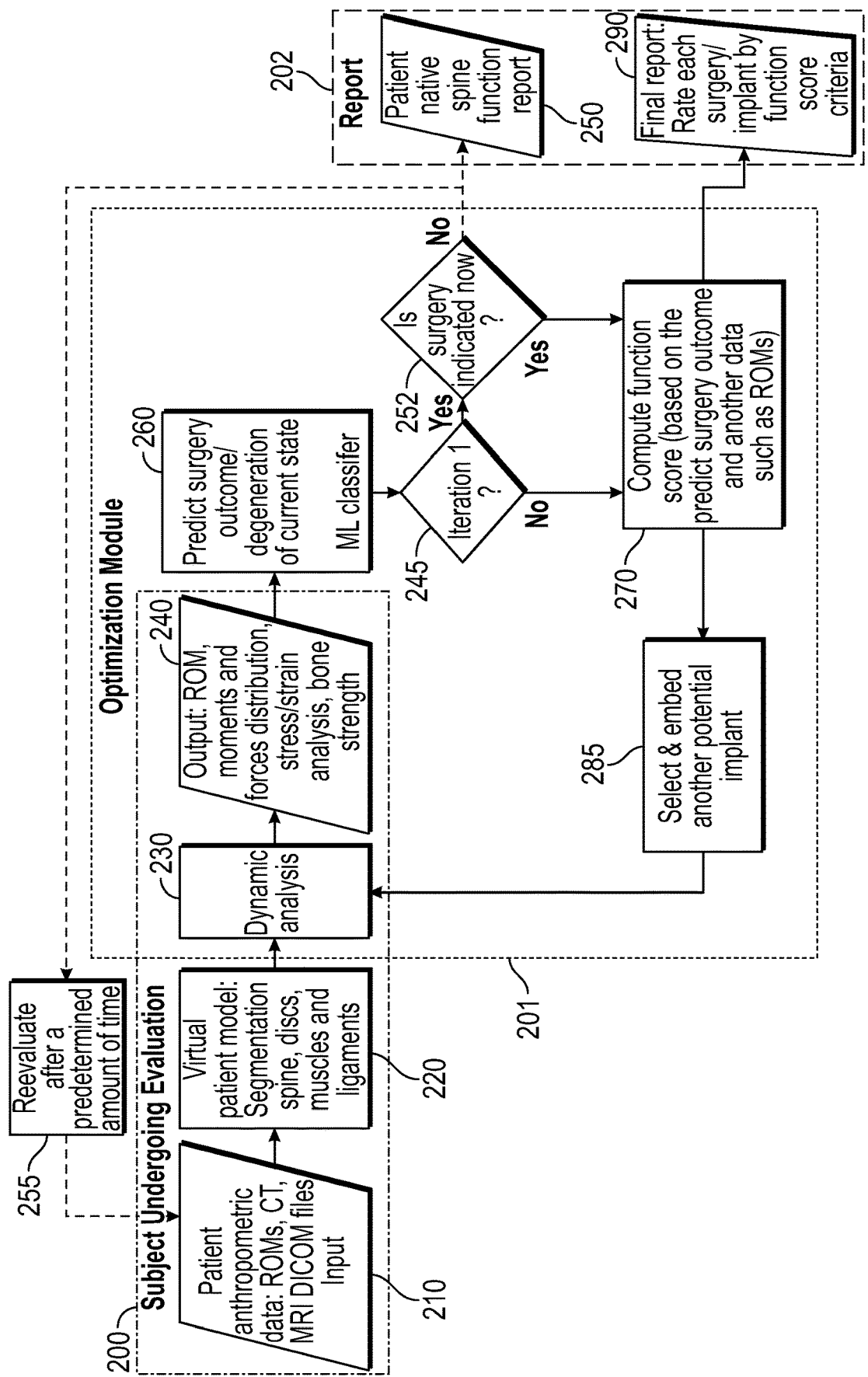
FIG. 2 shows a flow chart of steps taken in an exemplary implementation of the disclosed methods for selecting at least one of available implants.

Reference is now made to FIG. 2, showing an alternative implementation of the process illustrated in FIG. 1, in which one of a set of available implants is selected. Data for the subject under evaluation is represented by module 200, and comprises steps (model) 210, 220, 230, and 240, culminating in the dynamic analysis output 240, as further described in FIG. 3. The optimization module 201 encompasses both data on an individual subject (steps (model) 220, 230, and 240) and analysis of the subject's data in view of retrospective data on patients who previously underwent surgical correction similar to that planned for the subject under evaluation (machine learning algorithm 260, 270). The retrospective data is used in a machine learning algorithm 260 to classify the subject's biomechanical data comprising forces and moments, pressures, stresses, and strains, and to determine functional scores, on which planned surgical outcomes may be predicted. In step 252, an evaluation is made as to whether the subject's pathology warrants immediate surgical correction. This decision may be made by the surgeon, or by predetermined criteria input into the system. If not, the analysis could be repeated over time (step 245, iteration) by returning to module 200 and repeating the evaluation as needed until a decision is made to operate and which operation to perform. Such repeated evaluations over time allow a quantitative view of the clinical time course of the patient under evaluation and allow the system to predict when surgical repair is likely to be needed. The report provides information on the pathological parameters of the spine that necessitate an evaluation for surgical correction. The functional scores are based on post-operative data of successfully operated patients to determine the range of values of the relevant and important parameters required to reach a successful outcome, and those associated with clearly unsuccessful outcomes, as more fully described in FIGS. 6A and 6B. The functional scores are then evaluated to determine if they satisfy the predetermined criteria in step 270 using a given implant. If not, in step 285, the model is embedded with another surgery. If so, the surgery biomechanical parameters are included in the final report. Once all potential implants have been evaluated, a final report 290 is issued, taking into account the results of each iteration of the optimization module as well as the subject's native spine parameters 250.

In the machine learning algorithms, at least three possible classifications of a successful surgery outcome may be used, either alone or in combination. The three methods or categories of machine learning are binary classification (success/failure), multiclass classification (e.g., clear success, intermediate, clear failure), or regression for continuous scoring. If the values are within the acceptable range, the process will issue a final report 190, 290 with recommendations for performing the surgical procedure. Given that the subject under evaluation needs spinal correction for a condition affecting the biomechanics as well as the anatomy of the spine, it is expected that the subject will require at least one spinal implant to correct the spinal pathology. This requirement would be reflected in the function score criteria, which would not satisfy the functional criteria without planning the surgical correction. In such a case, from step 270, the process proceeds to step 285, in which selected sets of different implants are sequentially inserted into the biomechanical model of the patient's spine. The method is illustrated by the example of a case of a subject needing a single disc replacement to preserve motion, without fusion of multiple vertebral segments or correction of spinal deformity. Each possibly relevant implant undergoes dynamic analysis model 230 in the context of being implanted into the subject's spine. The dynamic analysis output 240, comprising ROMs, moments and force distribution, and stress and strain analyses of the subject's spine, is expected to change based on the biomechanical properties, size, shape, and stiffness of the specific implant being tested. Each implant is rated based on an equation that takes into account the important parameters and ranges of values for each parameter of the patient's spine with the implant virtually embedded, after defining the factors that contribute to favorable biomechanical outcomes postoperatively, as described above.

Whereas the example cited is for a single disc replacement, development of the method is generally applicable for predicting the success or failure of any number of spinal correction procedures or other operations based on dynamic analysis of the patient. Additionally, the method allows a decision as to whether surgery is indicated. Optimization of the planned spinal correction procedure is based on the score obtained in the previous steps, and may comprise optimization of geometry: i.e., the angle of the lordosis between two or more vertebrae; the type of implant: i.e., artificial intervertebral disc vs. interbody cage and intervertebral rods; the number of spinal levels to be operated; and the surgical approach: i.e., anterior, posterior, lateral, or other approach. For each implant tested, the prediction of the surgery outcome using the machine learning algorithmic 160, 260 will generate functional scores based on the output of the dynamic analysis in the context of previous patient outcomes, taking into account the parameters and range of values for each parameter associated with a successful outcome. After the optimization module 101, 201 has tested a set of potentially suitable artificial disc implants for the single vertebral level and patient characteristics, the implant is selected which provides the most optimal biomechanical correction and desired physiological properties within the constraints of the patient's dynamic analysis. The final report, either 190 or 290, is then issued detailing the results of the optimization module analysis.

In either FIG. 1 or FIG. 2, the surgical outcomes may be one or more parameters, or a combination of parameters. Examples of surgical outcome parameters comprise:

a) Patient reported outcome measures (PROMs): patients complete questionnaires related to pain, disability, and health-related quality of life (HRQOL) before and after treatment to track changes over time. Common PROMs include visual analog scales for pain (neck, arm, mid/low-back, leg, etc.) and the Oswestry disability index. PROMs are the gold-standard for patient-derived outcomes in spine-related care and research, and are often benchmarked using the minimum clinically important difference to discern good vs poor outcomes.

b) Radiographic alignment outcomes: coronal and sagittal radiographic images are used to measure various spinal alignment parameters reflecting aspects of global and region-specific alignment; these parameters are then referenced to ideal realignment goals. Like PROMs, alignment outcomes are tracked before and after surgery. Idealized realignment goals are derived from healthy, asymptomatic controls and can account for adjustment factors like severity of deformity, age, bone quality, bone morphology, etc. Severity of alignment deformities are often benchmarked by threshold values which have been shown to be associated with structural outcomes and with PROMs.

c) Functional outcome measures: a patient's physical function can be assessed using motion tracking technologies to provide objective measures of functional status and ability. Functional outcome measures are commonly derived for typical activities of daily life (ADLs) and can include kinematic, kinetic, and neuromuscular components. Like other outcome determinants, functional outcome measures are tracked before and after surgery and are commonly referenced to healthy control data.

Figure 3:
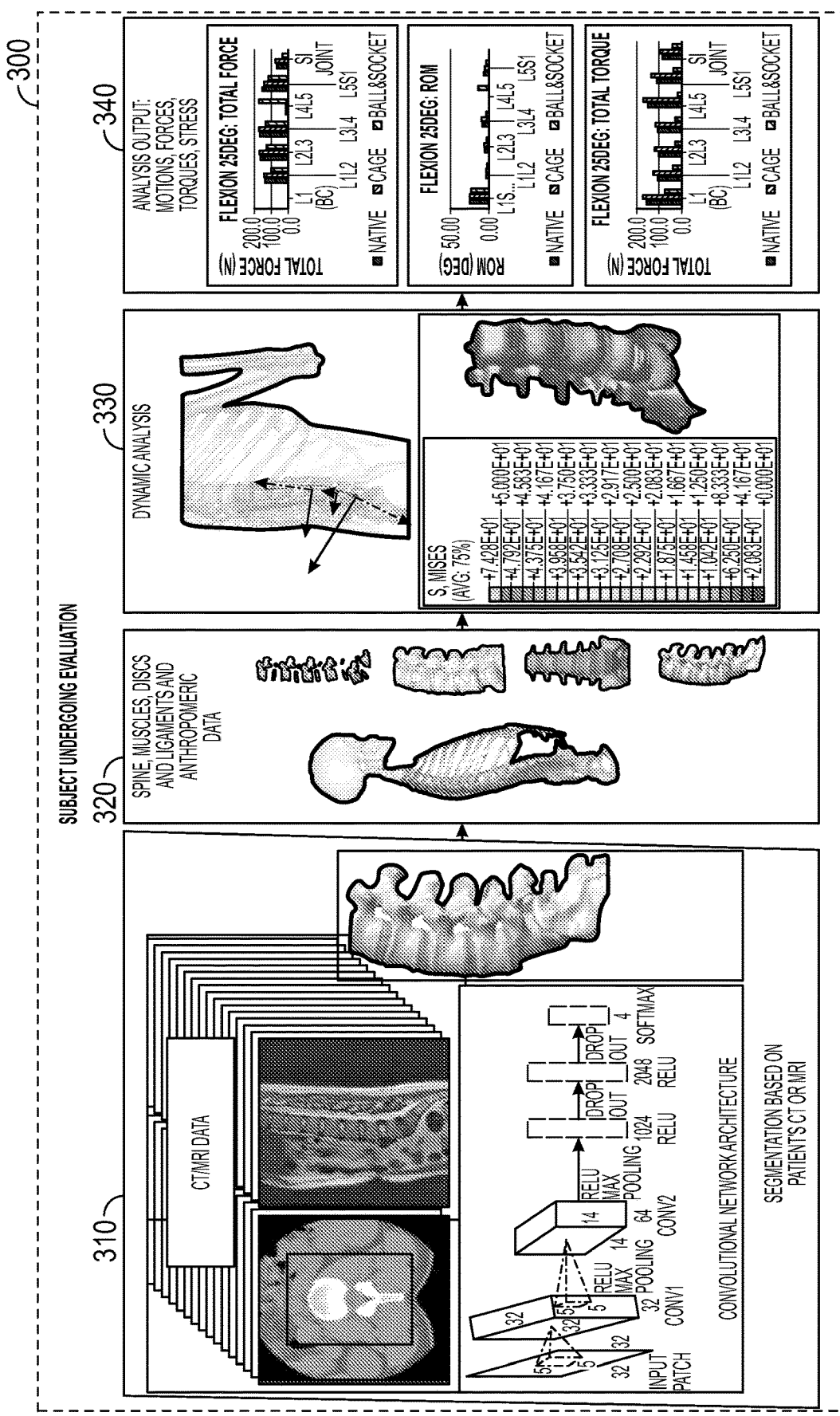
FIG. 3 details the steps in evaluating a specific subject in an exemplary implementation of the method.

Reference is now made to FIG. 3, which discloses further detail regarding the module 100, 200 regarding each subject's individual analysis. The module 300 is based on three-dimensional anatomical modeling of the spine and soft tissues, such as could be derived from automatic CT or MRI segmentation 310 with or without the use of convolution network architecture. The evaluation is performed on the upper body and analyzes elements such as: vertebrae, muscles, ligaments, discs and spinal range of motion; and anthropometric data. Anthropometric measurements are a series of quantitative, systematic measurements of the size, shape and composition of the human body comprising measurements of the muscle, bone, and adipose tissue. Several core elements of anthropometry are height, weight, body mass index (BMI), body circumferences (waist, hip, and limbs), and skinfold thickness. These comprehensive anatomical and physiological data 320 are used as the input to the dynamic analysis module 330.

The dynamic analysis module 330, virtual prediction and evaluation technology, can be based on at least one of, and typically both, musculoskeletal, finite element analysis, finite difference analysis, and finite volume analysis. The musculoskeletal model analysis, performed using, for example, AnyBody software, produces musculoskeletal models that simulate the human body working in concert with its environment. These simulations quantify forces, torques and motions inside the body, which are otherwise difficult to predict, measure, or determine. The goals of the biomechanical analyses comprise determining load-bearing requirements and optimizing implant positioning to improve the likelihood of surgical success. The finite element analysis, evaluates an implant in the context of the subject's spine, and predicts reactions to real-world forces, moments, stresses, strains, and other physical effects. Finite element analysis is used to predict whether or how soon a given implant will fail, or whether it will work in the way it was designed. These predictions may be based on the known materials properties for the material of which a specific implant is made, taking into account the stress acting on the spine-implant assembly. The output 340 of the subject analysis module comprises data on a set of potential implants, comparing the total forces, range of motion, and moments under various conditions, such as upright, spinal flexion and extension, right and left lateral bending, and right and left torsion. Such measurements are typically performed on each vertebral pair and joint, such as L1-L2, L2-L3, L3-L4, L4-L5, in the relevant region of the spine. The output of the biomechanical analysis for a given potential implant is provided in the context of its effect on both the joint into which it is to be implanted, e.g., L2-L3, as well as the predicted effect on the entire spinal region, e.g., L1-L5. As well, the output for each potential implant is compared to that for each implant in the set of implants being considered. These data comprise the analysis included in the native patient report (FIG. 1 step 150, FIG. 2 step 250). These same data are then subsequently used in the dynamic analysis steps of the dynamic analysis/model 130, 230, as further described in FIG. 5.

Figure 4:
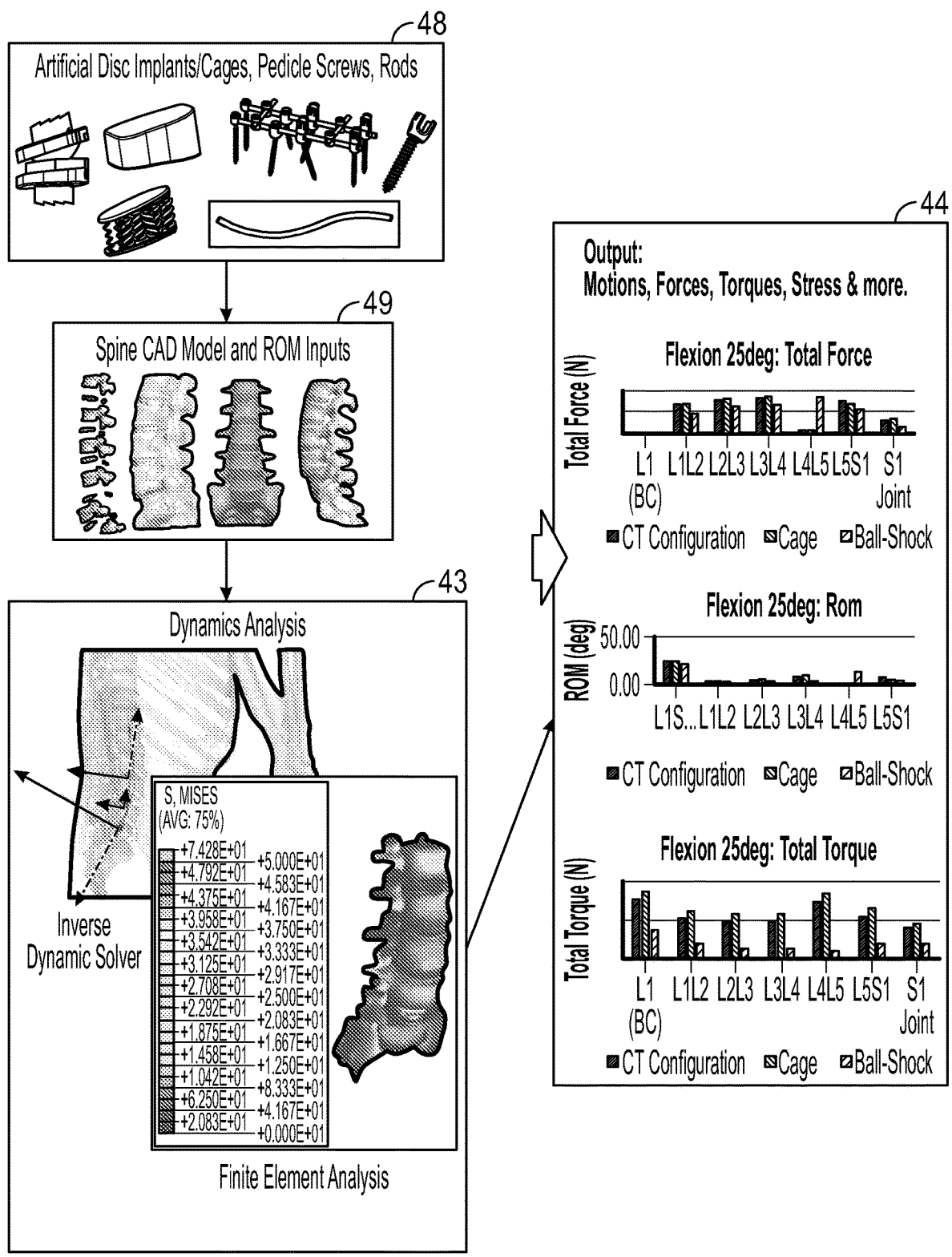
FIG. 4 illustrates exemplary output of the dynamic analysis of a subject's spine.

Reference is now made to FIG. 4, illustrating the step of the exemplary implementation of the disclosed methods, in which implants of a set of potential implants are individually and virtually embedded in the subject's three-dimensional spine model. At this point of the method, the DICOM images have been converted to a computer assisted drawing (CAD) model to generate a detailed two- or three-dimensional representation displaying the components of the subject's spine, including both bony elements and soft tissue such as discs, muscles, ligaments, and tendons. The CAD program creates individual three-dimensional elements of the spinal images to be used throughout the analytical process of the optimization module. A set of potentially suitable artificial discs 48 is selected for the intervertebral disc to be replaced. For a given subject, the selected set will be appropriate for the spinal level and other subject-specific considerations such as weight and dimensions of the native disc. Each potential disc from the set of potentially suitable artificial discs 48 will be embedded sequentially into the CAD model 49. Dynamic analysis 43 with finite elements and/or musculoskeletal model will be performed on each spine-implant configuration, and a full set of data output in step 44. These sample data correspond to those shown in FIG. 3 step output 340, comparing the motions, forces, moments, stress and strain analysis and more for each potentially suitable implant, whether an artificial disc, as in the artificial disc replacement procedure described, or other implants such as pedicle screws, intervertebral rods, or intervertebral cages in the case of a spinal fusion procedure. The analyses are performed in various positions of flexion, extension, bending, and torsion, depending on the indications of the specific subject's spinal pathology.

Figure 5B:
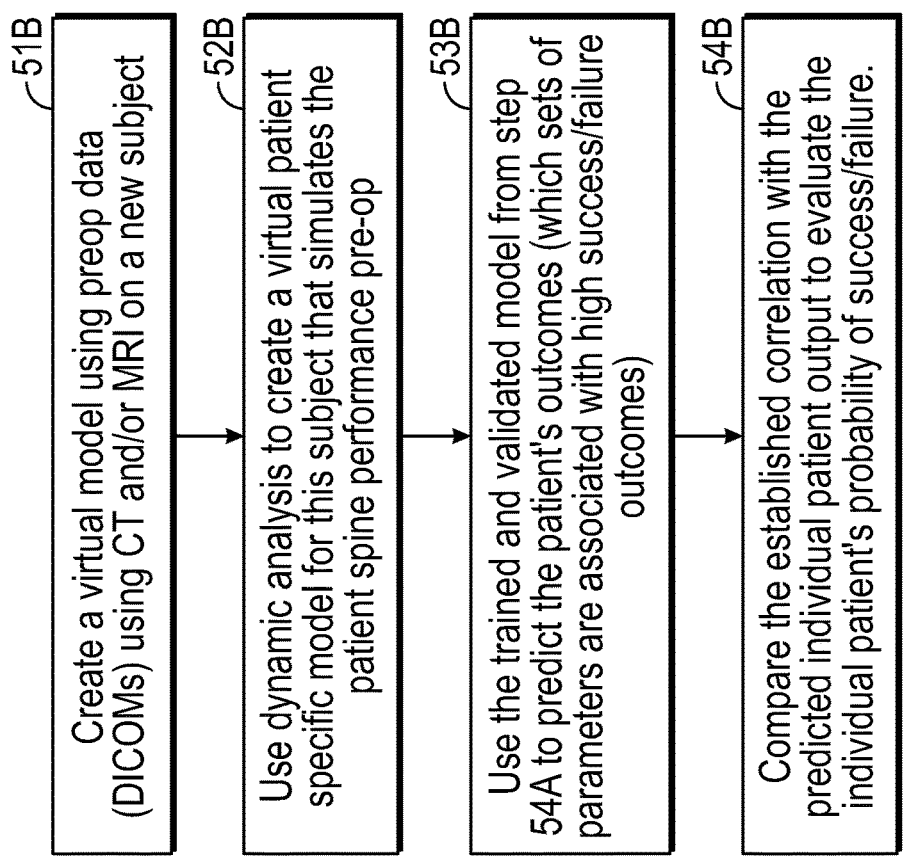
FIGS. 5A and 5B list the steps taken in an exemplary implementation of the disclosed methods for a reference population (FIG. 5A) and for a specific subject (FIG. 5B)
Figure 5A:
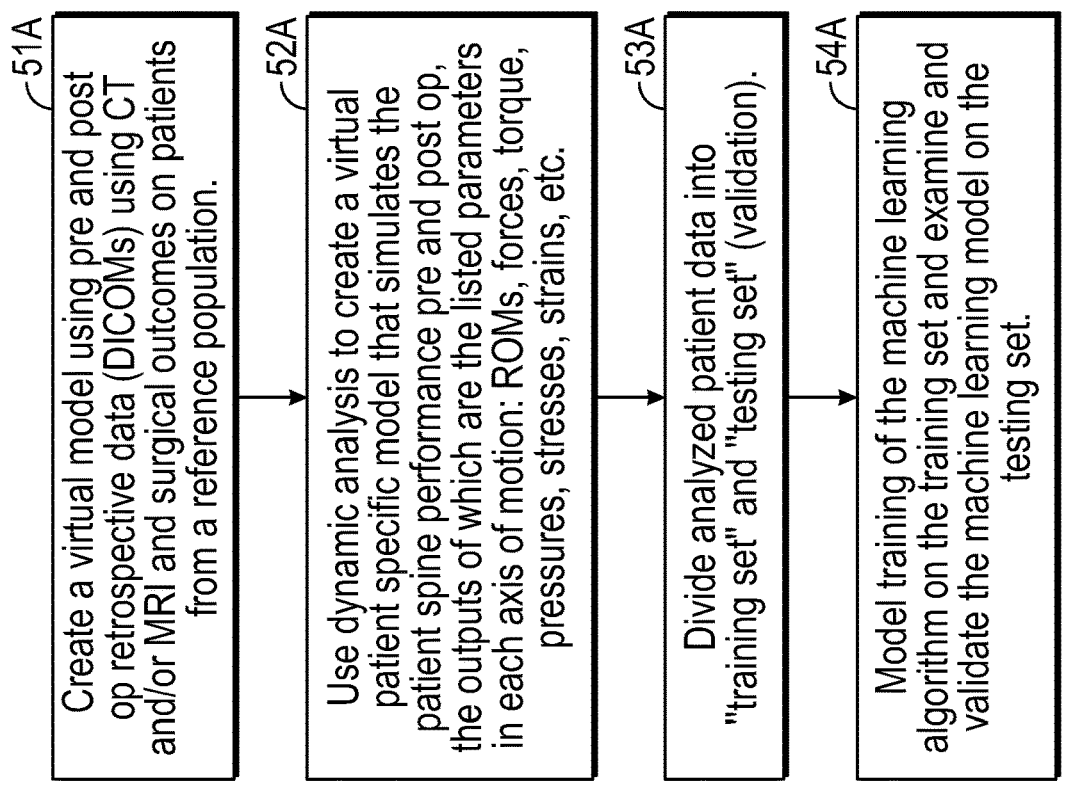
Figure 7:
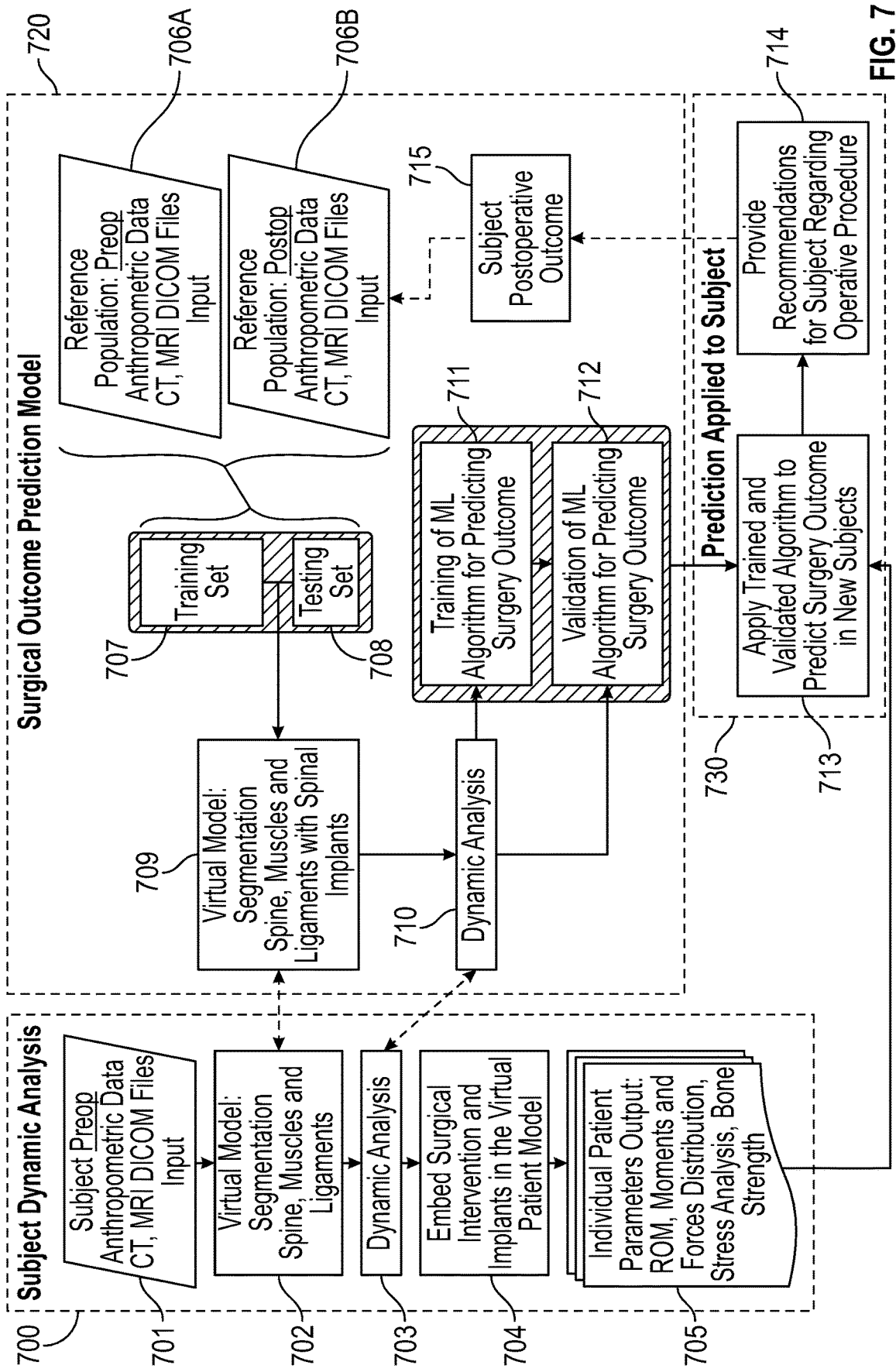
FIG. 7 shows a flow chart of steps used in training and using the machine learning algorithm for predicting surgical outcome.

Reference is now made to FIGS. 5A and 5B, flowcharts providing an overview of steps that can be used in a typical implementation of the optimization module (FIG. 1, 101, FIG. 2, 201), to be more extensively explained in FIG. 7. In FIG. 5A, in step 51A, a first model is created from a reference population using retrospective data (pre- and postoperative DICOMs) that include previous patients CT/MRI imaging data and surgical outcomes. In step 52A, dynamic analysis is used to create a virtual patient specific model using musculoskeletal model and/or finite element analysis that simulates each patient's spine performance pre- and post-operatively from the reference population. The outputs of this model are the listed parameters in each axis of motion: ROMs, forces, moments, pressures, strains, stresses, etc. In step 53A, patient data is divided into "training set" and "testing set" for validation, as will be further explained in FIG. 7. In step 54A, the machine learning algorithm using, e.g., classification or clustering, is trained on the "training set" and the machine learning model is validated on the "testing set". Concurrently and/or subsequently, as shown in FIG. 5B, in step 51B, a virtual model is created on a new, current subject using their specific preop CT/MRI data (DICOMs). In step 52B, dynamic analysis is used to create a virtual patient specific model (e.g., a CAD model) for this new subject that simulates the patient's preoperative spine performance. This model can then be used as an input to the method to decide if surgery is necessary. If surgery is decided, the model can be used to simulate a specific surgery for which the patient is under evaluation, using, e.g., the CAD model of step 52B. In step 53B, the trained and validated model from step 54A is used to establish the correlation between the model output and the patient's outcomes, i.e., which sets of parameters are associated with high success/failure outcomes. In step 54B, the established correlation is compared with the predicted individual patient output to evaluate the individual patient's probability of success/failure for a certain type of surgery.

Figure 6A:
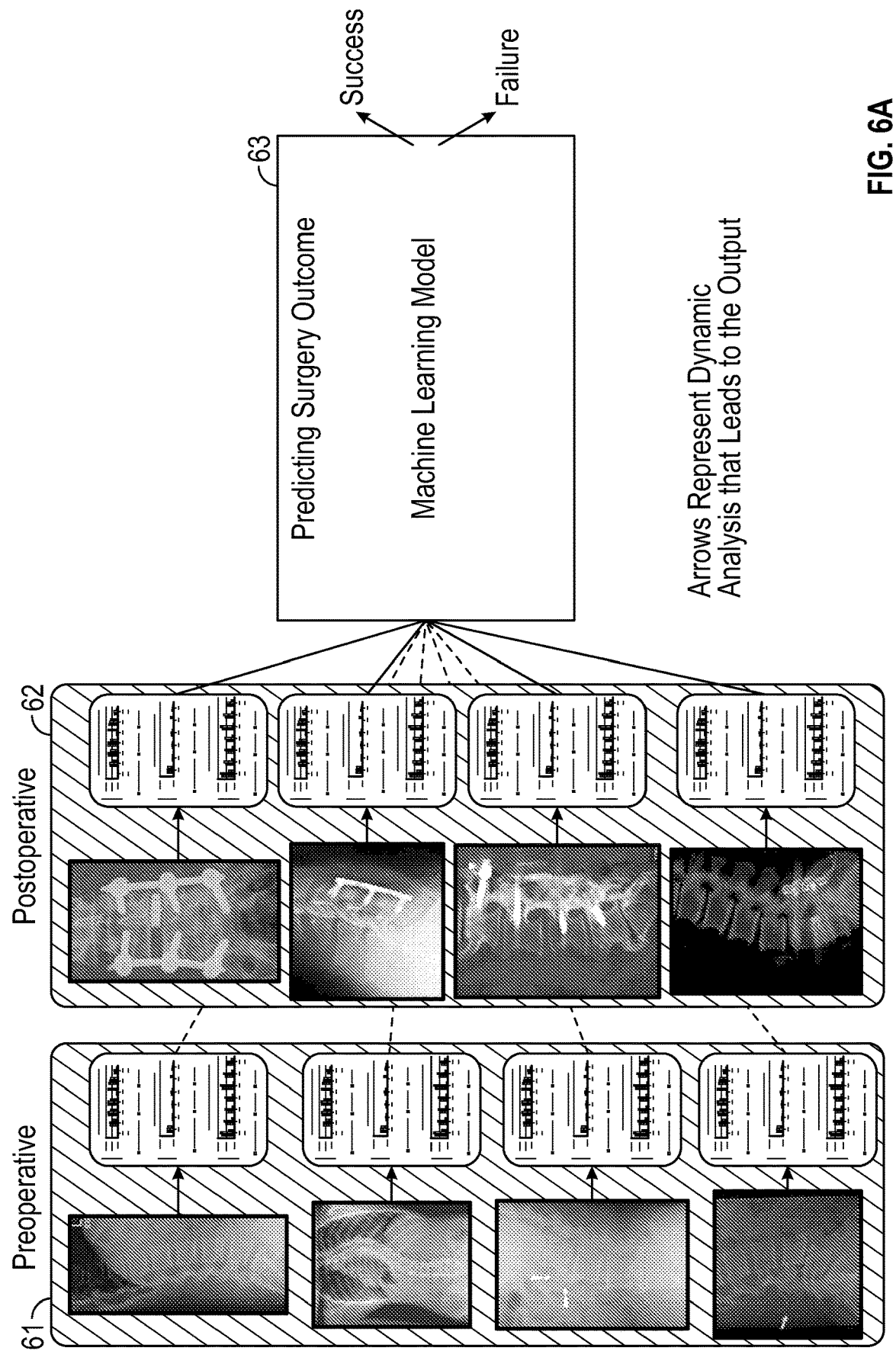
FIGS. 6A and 6B show the pre- and post-operative evaluation of individuals in a reference population used for predicting the probability of surgical success or failure.
Figure 6B:
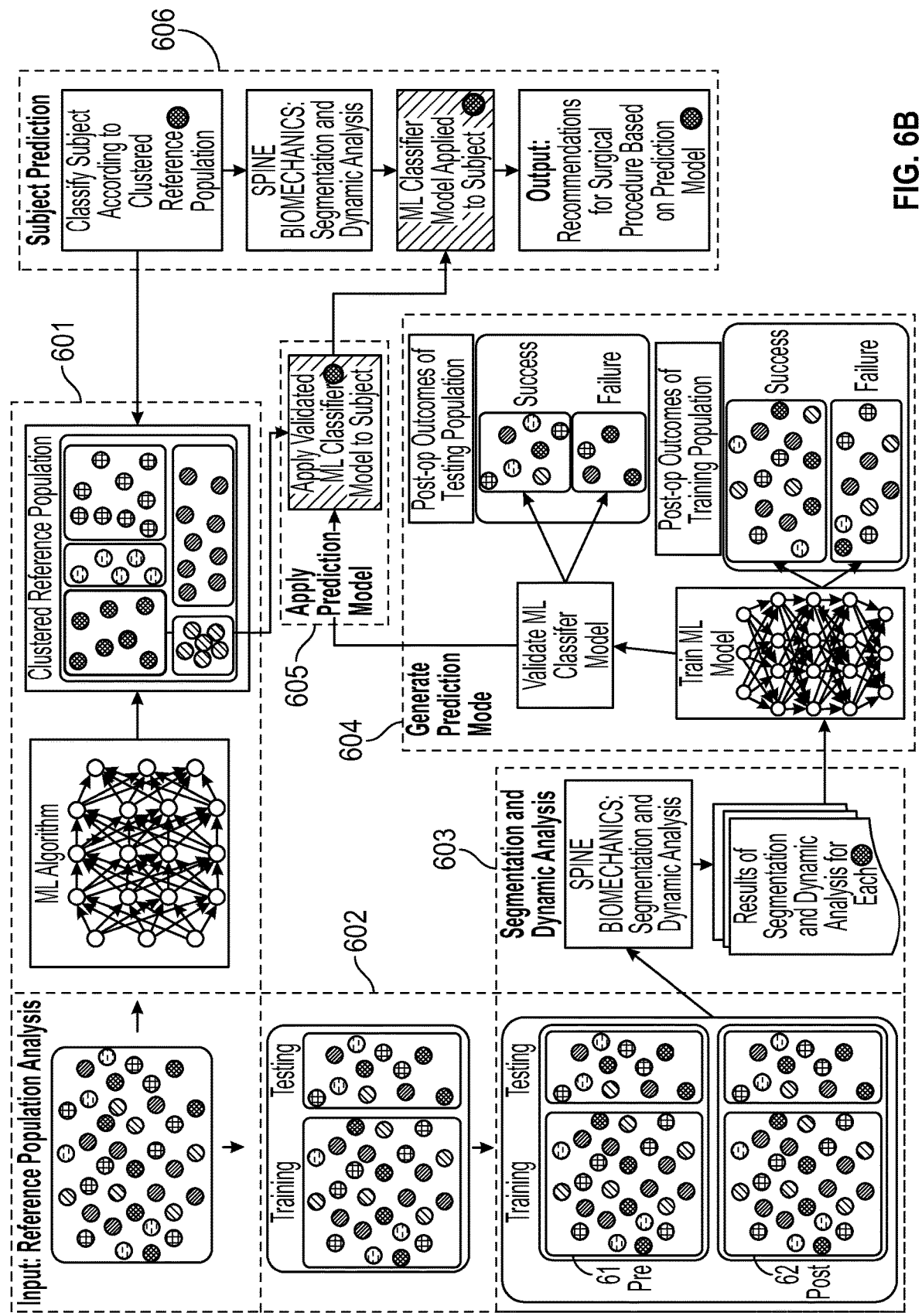

Reference is now made to FIG. 6A, illustrating development of the training model, as mentioned in FIG. 5A, step 54A, and as will be shown implemented in FIGS. 6B and 7, steps 711, 712. Clinical data are collected and analyzed from patients who have previously undergone corrective spinal surgery, derived from any number of sources. From these data, an equation is defined that takes into account the important biomechanical parameters and ranges of values for each parameter, wherein the relative importance of each relevant parameter is weighted, to define the biomechanical factors that contribute to a successful outcome in a particular patient having a specific disease. These data comprise both preoperative 61 and postoperative 62 imaging studies for each patient having undergone a spinal correction procedure. In the illustrated implementation of the disclosed methods, the patients are postoperative for spinal fusion procedures, each having been implanted with sets of pedicle screws and intervertebral rods for spine stabilization. The collected imaging data are analyzed according to the machine learning algorithms described above in FIGS. 3 to 5B, producing a three-dimensional CAD model of each patient's spine preoperatively and postoperatively, after the hardware has been implanted. The hardware is expected to impact the biomechanics of the spine, and thus both pre- and post-operative analyses may be used for comparison. In some cases, a separate analysis may be performed using only pre-operative or only post-operative data. The output of the dynamic analysis is represented by arrows 61 for pre-operative analysis and 62 for post-operative analysis. Each is input separately to the prediction machine learning algorithm 63.

From the dynamic analysis of FIG. 1, step 130 and FIG. 2, step (model) 230, typically comprising inverse dynamics and finite element analysis, the relevant biomechanical forces, moments, ranges of motion, and moments are calculated in upright positions. The inverse dynamics and finite element analysis portions of the algorithm are used to extrapolate to calculate the biomechanical parameters expected to be found in positions of, for example, flexion at a specific angle, for example, 25 degrees. The output of the dynamic analysis is then used as input into a machine learning algorithm 63 for prediction of surgery outcome. The prediction algorithm performs at least two functions. Firstly, it determines the relative success or failure of each patient's surgical spine correction procedure. The prediction score is, for example, the probability of success or failure obtained from the machine learning classifier. Secondly, it analyzes the biomechanical properties of each patient's preoperative and postoperative imaging parameters. With the output of both of these steps, the algorithm determines a correlation between the biomechanical properties associated with a successful outcome and those associated with failure. Because success or failure depends on multiple parameters and aspects, and encompasses a broad range of postoperative changes in the patient's condition, and because the subjective result may differ between the surgeon and the patient, a quantitative assessment of the definition of success must be determined.

In an exemplary implementation of the machine learning algorithm, the results of the training population will encompass results that may be defined by all criteria as 'optimal', i.e., successes, and those results that are by all criteria clearly failures. In between may lie a significant number of cases whose outcomes may be defined as partial successes, or successful in terms of one or more measured biomechanical or anatomical parameters, or in terms of patient satisfaction. Over time, the biomechanical parameters associated with greater success will become more clearly differentiated from those associated with a lower success rate.

By applying the predicted post-operative biomechanical parameters, the correlation between the biomechanical properties associated with a successful outcome and those associated with failure, this enables grading a predicted success of a planned spinal surgical procedure according to a predetermined rating. The grading of the predicted outcome of the planned spinal surgical procedure enables a health practitioner to take an appropriate decision to implement or not implement the planned surgical procedure so as to optimize a chance of a successful orthopedic surgery and/or to lower a risk for an unsuccessful orthopedic surgery for the subject.

A benefit of using this method over prior attempts to optimize the outcomes of spinal procedures is that it is based on a correlation of the biomechanical parameters of individuals who underwent past successful operations with a subject under current evaluation. By using biomechanical parameters as well as anatomical measurements, the surgeon is able to better predict and plan a spinal corrective procedure that will have the greatest chances of success. Because there is no way of predicting the postoperative biomechanical parameters in a subject before the operation, the use of a reference population allows a virtual comparison of pre- and post-operative biomechanical elements, with the intent of selecting the operation most likely to produce favorable biomechanical properties.

This principle and the method represented in FIG. 6A step (algorithm) 63 is illustrated in more detail in FIG. 6B, showing an exemplary reference population and the manner in which the disclosed methods may be applied for the purpose of predicting surgical outcome and selection of the procedure and implants most likely to produce a favorable long term result. The exemplary method is comprised of several independent and interconnected modules 601 to 606. Module 601 performs a clustering machine learning algorithm on the pre-operative characteristics of each individual in the reference population to identify patients with similar anthropometric and biophysical parameters. While the exemplary machine learning algorithm in module 601 illustrates a neural network, a number of different methods may be used for performing clustering. Module 602 randomly assigns the patients in the reference population into either training or testing subsets. Module 603 applies segmentation and dynamic analysis to the pre- and post-operative imaging data of each individual in the reference population, both training and testing subsets. In module 604, the prediction model is generated to correlate biomechanical parameters with successful vs. unsuccessful surgical outcomes using either classification or regression machine learning. The model is trained on the training population and validated on the testing population, as will be further elaborated in FIG. 7. Once the model has been trained and validated, in module 605 it may be applied to a new patient or subject undergoing pre-surgical evaluation. In module 606, the new subject is first classified according to the clustered reference population which comprises the outcome of module 601. Independently, the preoperative images are subjected to segmentation and dynamic analysis, as described in FIG. 3, after which the prediction model from module 605 is applied to the subject's biomechanical parameters. The intended, selected surgical procedure will be performed virtually in the patient's virtual model, using biomechanical representations of the selected implants. The final output of the method at 606 is recommendations for a surgical procedure using implants predicted from the retrospective analysis of the reference population to optimize the long term outcome of the selected procedure.

Reference is now made to FIG. 7, illustrating the steps involved in an exemplary implementation of the disclosed methods, wherein a given subject's data is evaluated by the dynamic analysis quantitative model 700, and subsequently by the trained and validated surgical outcome prediction model 720, thereby integrating all of the methodology described hereinabove. In step 701, the subject's anthropometric data, CT, MRI, and x-ray files as input. In step 702, the input data is analyzed and a virtual model is created, as described in FIG. 1, step 120, by performing segmentation of the bone and soft tissue, i.e., spine, muscles, and ligaments. In step 703, the output of step 702 undergoes dynamic analysis as in steps 130, 230, and 330, which includes embedding surgical intervention and/or implants in the virtual model created in step 704, resulting in individual output parameters for the patient under evaluation, comprising ROM, moments and force distributions, stress and strain analysis, bone strength, as shown in step 705. The output (output parameters) from step 705 is used as input to step 713, where the trained and validated algorithm for predicting the surgical outcome is applied to this output, as will be described herewith below.

In an embodiment, the module of box (surgical outcome prediction model) 720 incorporates the methodology by which the system achieves the prediction of the surgical outcome, for application to the individual patient output parameters from step 705 of the subject dynamic analysis module 700. This procedure is initially performed when the system is set-up, and is updated continuously as more data from more patients is streamed through it, from which the accuracy increases as the module continues learning. In steps 706A and 706B, a reference population is selected from records of patients who have previously undergone surgical procedures for spinal correction. These patient records comprise the same type of information that is collected from the specific patient under evaluation in step 701, except that the data comprise both pre-operative steps (706A) and postoperative (706B) imaging and anthropometric results. Such records may be obtained from health care organizations, hospitals, insurance companies, or private surgeons who have agreed to pool their resources. In any case, the reference population should derive from a similar geographical or genetic population as the subject under evaluation. For different clinical problems, it may be necessary to train different machine learning models, such that each clinical pathology is trained on data specific to the problem. A large proportion of the reference population is chosen at random to comprise the training set 707, whereas the remaining records are set aside to comprise the testing set 708. The data from the training set 707 undergo segmentation in step 709, comparable to that performed in step 702 on the specific subject data, the output of which is used as input into the dynamic analysis module in step 710, comparable to the dynamic analysis performed in step 703. The output of step 710 is input into the machine learning model 711 to analyze outcomes of the surgical procedures that were performed on the individuals in the training set 707, with regard to the calculated biomechanical parameters in the dynamic analysis 710.

Therefore, as it is appreciated from the above paragraphs, the dynamic analysis method allows to predict a success/failure of a planned spinal surgical procedure. The method is implemented on a computer processor. The computer processor receives at least one correlation between one of post-operative and pre-operative biomechanical parameters and outcome of the spinal surgical procedure for each one of at least some members of a reference population (retrospective data). A computer processor then generates a virtual biomechanical model of a subject under evaluation for a spinal surgery using at least one of pre-operative imaging and anthropometric data of the subject. The computer processor derives, pre-operative biomechanical parameters from the generated virtual biomechanical model of the subject; and simulates the planned spinal surgical procedure to predict post-operative biomechanical parameters of the subject using the generated virtual biomechanical model of the subject. The computer processor then applies to at least one of the derived pre-operative biomechanical parameters and the predicted post-operative biomechanical parameters of the subject the at least one correlation to grade a predicted outcome of the planned spinal surgical procedure according to a predetermined rating. The applying of the at least one correlation enables grading a predicted outcome of the planned spinal surgical procedure according to the predetermined rating. The grading of the predicted outcome of the planned spinal surgical procedure enables a health practitioner to take an appropriate decision to implement or not implement the planned surgical procedure so as to optimize a chances of a successful orthopedic surgery and/or to lower a risk for an unsuccessful orthopedic surgery for the subject.

In the above embodiment, biomechanical data of the reference population that is used to train the machine learning model 711 is selected from records of patients who have previously undergone surgical procedures for spinal correction. In another embodiment, the biomechanical data of a healthy reference population and/or one or more subjects that have undergone a successful or failed surgery is used to train the machine learning model 711 by deriving the biomechanical data from a simulation system and/or musculoskeletal model to determine at least one target value (or a range of normal target values) for each spine segment through the spine motion. For example, determining the range of normal intradiscal pressure at each of the intravertebral discs at 30 degrees flexion in a population of 60 to 65-year-old healthy females, etc. In an embodiment, the data (i.e., pre- or post-operative biomechanical parameters) can be normalized by BMI/body habitus, for example, or any other normalizing methodology. This data can then serve as the target which the correction procedure aims to achieve. For example, the target can be compared to a predicted outcome of a planned orthopedic and/or spinal surgery that is based on at least post-operative biomechanical parameters of a subject under evaluation for an orthopedic and/or spinal surgery using a generated virtual biomechanical/musculoskeletal model of the subject. If the predicted outcome of the planned orthopedic and/or spinal surgery for the subject overlaps with the target or range of values, a health practitioner might decide to proceed with the planned orthopedic and/or spinal surgery on the subject. However, if the predicted outcome of the planned orthopedic and/or spinal surgery for the subject does not overlap with the target or range of values, a health practitioner might decide to go with an alternative orthopedic and/or spinal surgery or no surgery at all.

In an embodiment, as it is appreciated from the above paragraphs, there is provided a method for planning an orthopedic surgical procedure. The method is implemented by a computer processor. The method includes receiving, by the computer processor, at least one target for a planned orthopedic surgical procedure, the at least one target relating to biomechanical parameters being derived from a virtual biomechanical model of one or more healthy subjects and/or one or more subjects that have undergone a successful or failed surgery and/or existing reference data for one or more of bones, ligaments and muscles comprising a spine of a plurality of previous patients that had a spinal condition; generating a virtual biomechanical model of a subject under evaluation for an orthopedic surgery, by a computer processor, using at least one of pre-operative imaging data and anthropometric data of the subject; simulating, by the computer processor, the planned orthopedic surgical procedure to predict post-operative biomechanical parameters of the subject using the generated virtual biomechanical model of the subject; and applying, by the computer processor, to the predicted post-operative biomechanical parameters of the subject the at least one target to compare a predicted outcome of the planned orthopedic surgical procedure that is based on the post-operative biomechanical parameters of the subject with the at least one target. The applying to the predicted post-operative biomechanical parameters of the subject, the at least one target, enables grading a predicted outcome of the planned orthopedic surgical procedure according to a predetermined rating. The grading of the predicted outcome of the planned orthopedic surgical procedure enables a health practitioner to take an appropriate decision to implement or not implement the planned surgical procedure so as to optimize a chance of a successful orthopedic surgery and/or to lower a risk for an unsuccessful orthopedic surgery for the subject.

In an embodiment, the computer processor further derives pre-operative biomechanical parameters from the generated virtual biomechanical model of the subject. In an embodiment, the computer processor normalizes the post-operative biomechanical parameters of the subject and/or the predicted outcome to the anthropometric data of the subject or normalizes the post-operative biomechanical parameters of the subject and/or the predicted outcome to the pre-operative biomechanical parameters of the subject.

After the model has been established and successful outcomes distinguished from failed outcomes, as in FIG. 6A step algorithm 63, and in FIG. 6B, the model is validated using the data from the testing set 708, which too undergoes segmentation in step 709 and dynamic analysis in step 710. The testing set is evaluated using the machine learning algorithm developed in step 711. In step 712, the output from steps 709, and 710, as applied to the data from testing set 708, is used to validate the results obtained in step 711.

Once the model has been validated and performs with a predetermined level of accuracy, the algorithm may be applied to the current subject needing spinal correction (see prediction module 730). In step 713, the output from the subject under evaluation from step 705 is input to the mature model and evaluated. From this analysis using the prediction algorithm, recommendations for surgical spinal correction of the subject are generated in step 714. These recommendations take into account the results of the model analysis on the reference population, such that the subject is matched to those prior patient results having similar biomechanical parameters and successful outcomes. As more patients are analyzed, higher accuracy and better performance of the algorithm and model is expected. In some implementations of the disclosed methods, the postoperative anthropometric and imaging data is collected in step 715 and entered into the reference population. In this way, the system is configured to continually update the recommendations and improve outcomes for future cases.

A correlation is expected between the biomechanical parameters associated with a successful outcome and the type of surgical intervention performed to result in the successful outcome, such that those interventions can be selected or recommended for a subject undergoing evaluation for spinal correction. By matching the biomechanical parameters of a current subject with those of patients in the training and testing sets who were operated with successful outcomes, the surgeon is able to select one or more possible procedures most likely to result in a successful outcome for the subject under evaluation.

Figure 8:
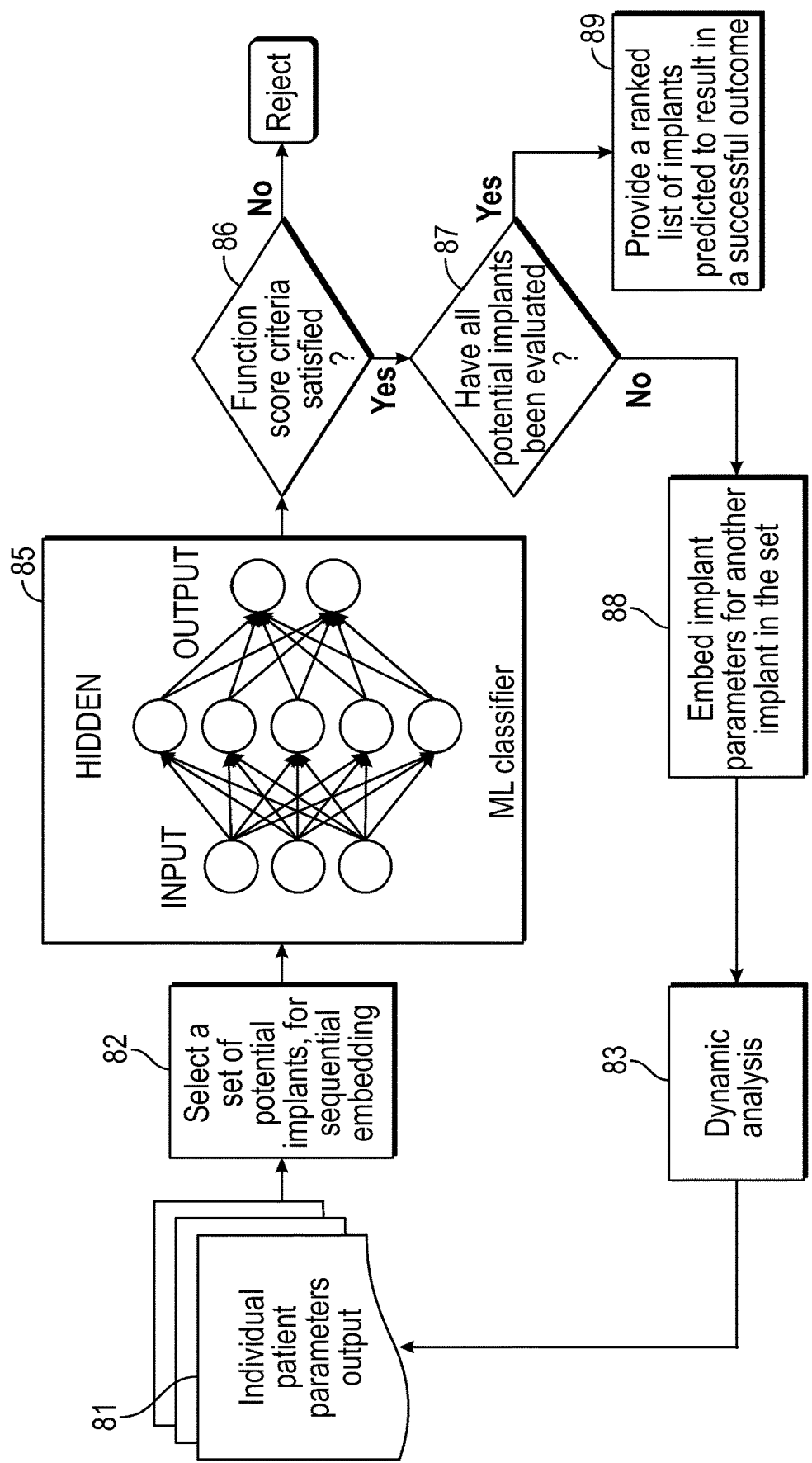
FIG. 8 illustrates details of the subject's preoperative analysis using an implementation of some of the disclosed machine learning algorithms.

Reference is now made to FIG. 8, showing how potential implants are evaluated for a subject. An individual patient's parameters 81 are analyzed, based on which a set of potential implants is selected in step 82. In the machine learning prediction algorithm 85, the analyzed patient spine biomechanical parameters are input into the machine learning prediction algorithm 85 in the context of one of the potential implants embedded. The algorithm predicts the likelihood of success for a given potential implant, and, in function score criteria test 86, the system determines whether the suggested implant fulfills its expected functions. In step 87, the system determines whether all potential implants have been evaluated. If so, the system in step (report) 89 provides a ranked list of implants predicted to result in a successful outcome, and makes recommendations for the surgical spinal correction. After running the machine learning prediction algorithm 85 on the subject's analyzed data 81, the system evaluates whether the functional criteria step 86 would be satisfied for the recommended surgical correction by comparing the functional scores of the patient with the biomechanical factors and values defined in FIG. 6A as being consistent with a successful surgical outcome. The set of favorable biomechanical parameter values have been determined by analysis of past surgical operations on a reference population. If so, the specific selected procedure is accepted and the system proceeds to recommending the surgical procedure 89. If the function score criteria are not satisfied, indicating that the selected surgical implant is predicted to not fulfill the desired biomechanical forces, moments in flexion, extension, lateral bending and axial rotation, the system proceeds to step 88 to select another implant with improved geometry and allowed motion. In step 83, the system performs dynamic analysis and reevaluates the subject's biomechanical properties with the implant characteristics selected in step 88. This iterative loop may be performed until all potential implants have been evaluated, upon which the system provides a report 89 ranking the potential implants according to the likelihood of producing a successful surgical outcome in terms of biomechanical forces.

Figure 9:
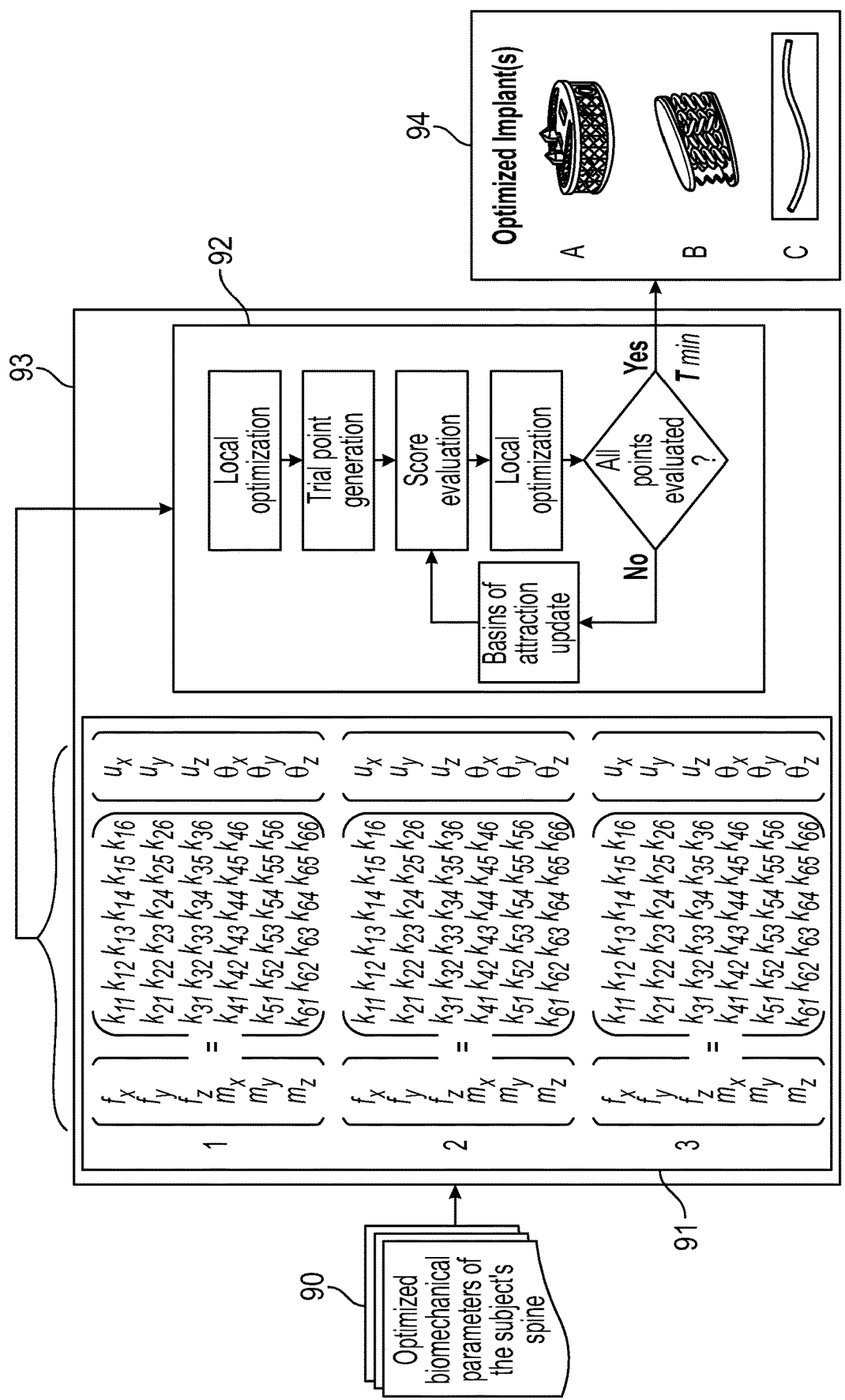
FIG. 9 shows output of biomechanical analysis of possible spinal implants, allowing selection of the implant(s) most likely to allow a successful outcome in the subject.

Reference is now made to FIG. 9, showing how a personalized implant may be generated for a specific patient using the disclosed methods. An optimized implant for the subject under evaluation can be selected once the biomechanical parameters have been determined for each potential implant embedded in the context of the subject's spine, as described in FIGS. 2 to 4. These parameters comprise optimized ranges of motion in various positions of flexion, extension, lateral bending, axial rotation, forces, and moments, as in step 90. The output of step 90 is used as input to a method 93 of generating a set of stiffnesses 91 for each potential implant, which are analyzed at step 92 as per the mathematical principles described in WO 2020/121054A2 "Motion preservation by an artificial spinal disc," published Jun. 18, 2020, by O. David and M. Shoham, and assigned to the Technion Research & Development Foundation, LTD. Based on the output of the modules in 93, mathematical descriptions of the geometric and biomechanical parameters of an optimal implant or set of implants with the required range of motions under specific forces and moments can be generated, at step 94. The mathematical values are used to build a specific implant, e.g., by three-dimensional printing. In an exemplary implementation, the optimized implant or implants comprise at least one artificial disc with a defined geometry and spring array, or a set of intervertebral cage(s) and rods for a spinal fusion, that match the required forces and allowable flexion for the patient to be treated.

Figure 10:
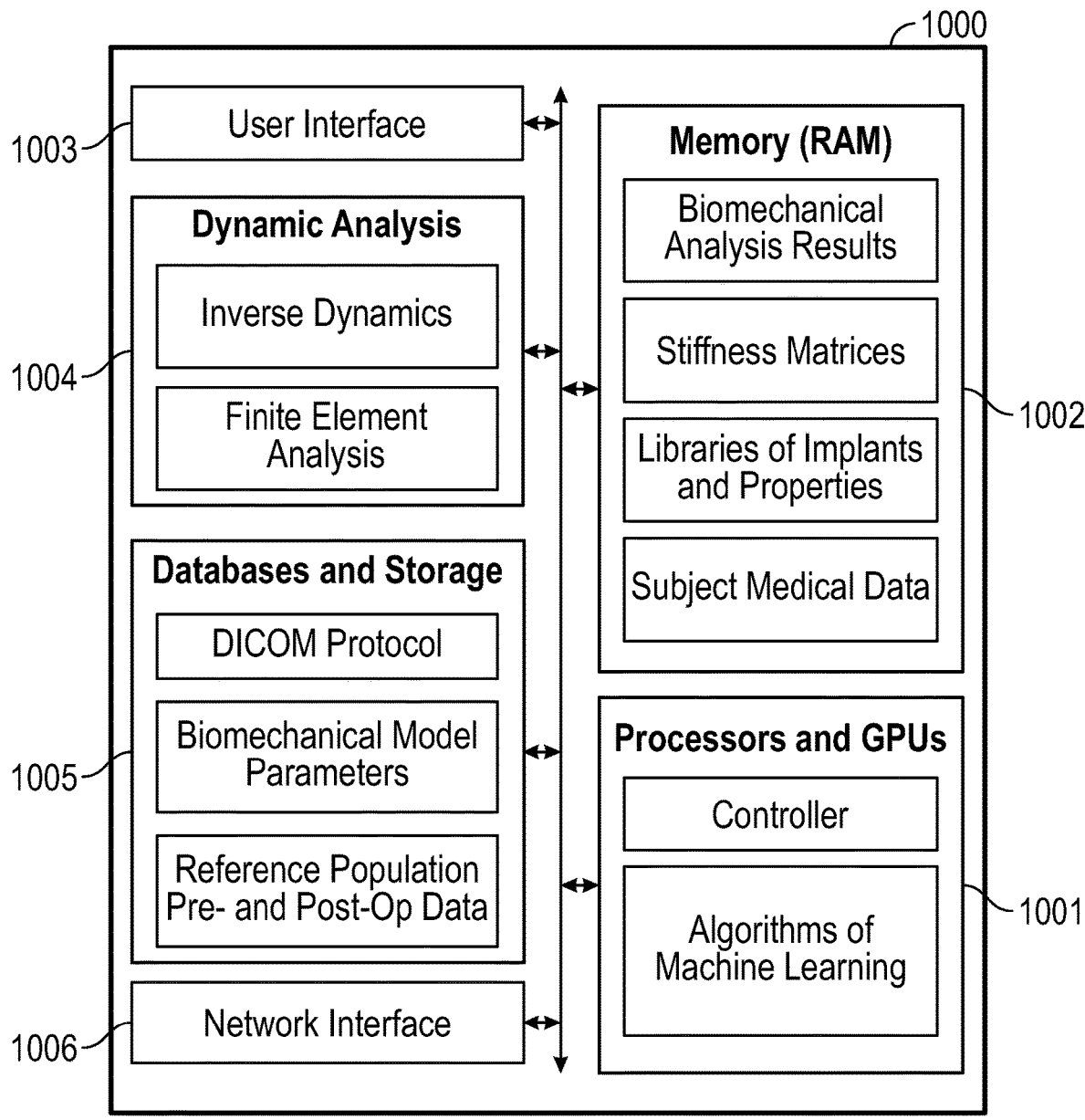
FIG. 10 illustrates a typical system used to implement the disclosed methods.

Reference is now made to FIG. 10, diagramming an illustrative system 1000 for implementing embodiments of the disclosed methods. The system 1000 comprises at least one processor and processor unit 1001, random access memory (RAM) 1002, a user interface 1003, a network interface 1006, a unit for dynamic analysis 1004, and at least one database or cloud storage 1005. The processor unit 1001 further comprises algorithms for machine learning, as described herewith above, and a controller. The RAM 1002 includes the stiffness matrices (shown in FIG. 9), libraries of implants having various characteristics and properties suitable for various spinal levels and surgical indications, results of the biomechanical analyses, and subject medical data and imaging studies. The database or cloud storage 1005 comprises DICOM protocols, biomechanical model properties, and reference population pre-operative and post-operative data (shown in FIG. 7). The dynamic analysis 1004 comprises the coding required to perform the inverse dynamics and finite element analysis.

As it can be appreciated from the above paragraphs there is provided a method for predicting the outcome of a planned spinal surgical procedure. The method includes: a) analyzing pre-operative biomechanical parameters from at least one of pre-operative imaging and anthropometric data, of a member of a reference population; b) analyzing biomechanical parameters after performance of a spinal surgical procedure on the member from at least one of post-operative imaging and post-operative anthropometric data of the member; c) grading the success of the spinal surgical procedure for the member of the reference population, according to a predetermined rating; d) repeating steps a) to c) on additional members of the reference population; e) determining at least one correlation between the pre-operative biomechanical parameters and the post-operative biomechanical parameters for each one of at least some of the members of the reference population; f) analyzing pre-operative biomechanical parameters from at least one of pre-operative imaging and anthropometric data, of a subject under evaluation for a spinal surgical procedure; g) simulating the surgical intervention and analyzing predicted post-operative biomechanical parameters of the subject under evaluation for spinal surgical procedure; h) applying the at least one correlation determined in step e) to at least one of steps f) and g) to grade the predicted outcome of the planned spinal surgical procedure according to the predetermined rating. The method further includes applying to the predicted post-operative biomechanical parameters, the at least one correlation, enables grading the predicted success of the planned spinal surgical procedure according to the predetermined rating. The grading of the predicted outcome of the planned spinal surgical procedure enables a health practitioner to take an appropriate decision to implement or not implement the planned surgical procedure so as to optimize a chance of a successful orthopedic surgery and/or to lower a risk for an unsuccessful orthopedic surgery for the subject.

As is can be further appreciated from the above paragraphs there is also provided a method for predicting a success of a planned spinal surgical procedure, comprising: a) analyzing pre-operative biomechanical parameters of a member of a reference population from at least one of pre-operative imaging and pre-operative anthropometric data; b) analyzing post-operative biomechanical parameters from at least one of post-operative imaging and post-operative anthropometric data, after the member has undergone a spinal surgical procedure; c) grading the success of the spinal surgical procedure according to a predetermined rating; d) repeating steps a) to c) on additional members of the reference population; e) determining at least one correlation between at least one of the pre-operative and the post-operative biomechanical parameters, and success of the spinal surgical procedure, for each one of at least some of the members of the reference population; f) analyzing pre-operative biomechanical parameters from at least one of pre-operative imaging and anthropometric data, of a subject under evaluation for a spinal surgical procedure; g) using at least one of the pre-operative imaging and anthropometric data to generate a virtual biomechanical model of the subject; and h) applying to at least one of the analyzed pre-operative biomechanical parameters and the predicted post-operative biomechanical parameters of the subject, the at least one correlation determined in step e), to grade a predicted outcome of the planned spinal surgical procedure according to the predetermined rating.

Therefore, in general for example in an embodiment of the present disclosure, there is provided a method for predicting a success of a planned spinal surgical procedure, the method being implemented by a computer processor. The method includes receiving, by the computer processor, reference data. The reference data can include: (a) at least one target for a planned orthopedic surgical procedure, the at least one target relating to biomechanical parameters being derived from (i) a virtual biomechanical model of one or more healthy subjects, (ii) one or more subjects that have undergone a successful or failed surgery, and/or (iii) existing reference data for one or more of bones, ligaments and muscles comprising a spine of a plurality of previous patients that had a spinal condition, and/or (b) at least one correlation between at least one of post-operative and pre-operative biomechanical parameters and outcome of the orthopedic surgical procedure for each one of at least some members of a reference population. For example, existing reference data comprises data in a book, data in a reference document, and/or data from an online data source.

The method further includes generating, by the computer processor, a virtual biomechanical model of a subject under evaluation for an orthopedic surgery, by a computer processor, using at least one of pre-operative imaging data and anthropometric data of the subject; simulating, by the computer processor, the planned orthopedic surgical procedure to predict post-operative biomechanical parameters of the subject using the generated virtual biomechanical model of the subject; and applying, by the computer processor, to the predicted post-operative biomechanical parameters of the subject the reference data. Applying to the predicted post-operative biomechanical parameters of the subject, the reference data, enables grading a predicted outcome of the planned orthopedic surgical procedure according to a predetermined rating. The grading of the predicted outcome of the planned orthopedic surgical procedure enables a health practitioner to take an appropriate decision to implement or not implement the planned surgical procedure so as to optimize a chance of a successful orthopedic surgery and/or to lower a risk for an unsuccessful orthopedic surgery for the subject.

In another embodiment of the present disclosure, there is provided a method for predicting a success of a planned orthopedic surgical procedure, the method being implemented by a computer processor. The method includes receiving, by the computer processor, reference data, generating, by the computer processor, a virtual biomechanical model of a subject under evaluation for an orthopedic surgery, by a computer processor, using at least one of pre-operative imaging data, post-operative imaging data and anthropometric data of the subject to generate a virtual biomechanical model of the subject under evaluation, simulating, by the computer processor, the planned orthopedic surgical procedure including incorporating a simulated implant(s) into the generated virtual biomechanical model of the subject, comparing, by the computer processor, results of the simulation with the reference data, and determining, by the computer processor, whether stresses on the implant(s), bones, ligaments and muscles are exceeding a failure point of the implant(s) based on the reference data. In an embodiment, the reference data can include at least one of (a) reference data from one or more subjects that have undergone a successful or failed surgery, and (b) existing reference data for one or more of bones, ligaments and muscles comprising a spine of a plurality of previous patients that had a spinal condition. In another embodiment, the reference data can include at least one of data in a book, data in a reference document, and data from an online data source relating to one or more of (i) bones, ligaments and/or muscles of a human patient, (ii) structural features of one or more implants, (iii) material properties of one or more implants, and (iv) forces exerted on a spine of a human patient.

Figure 11:
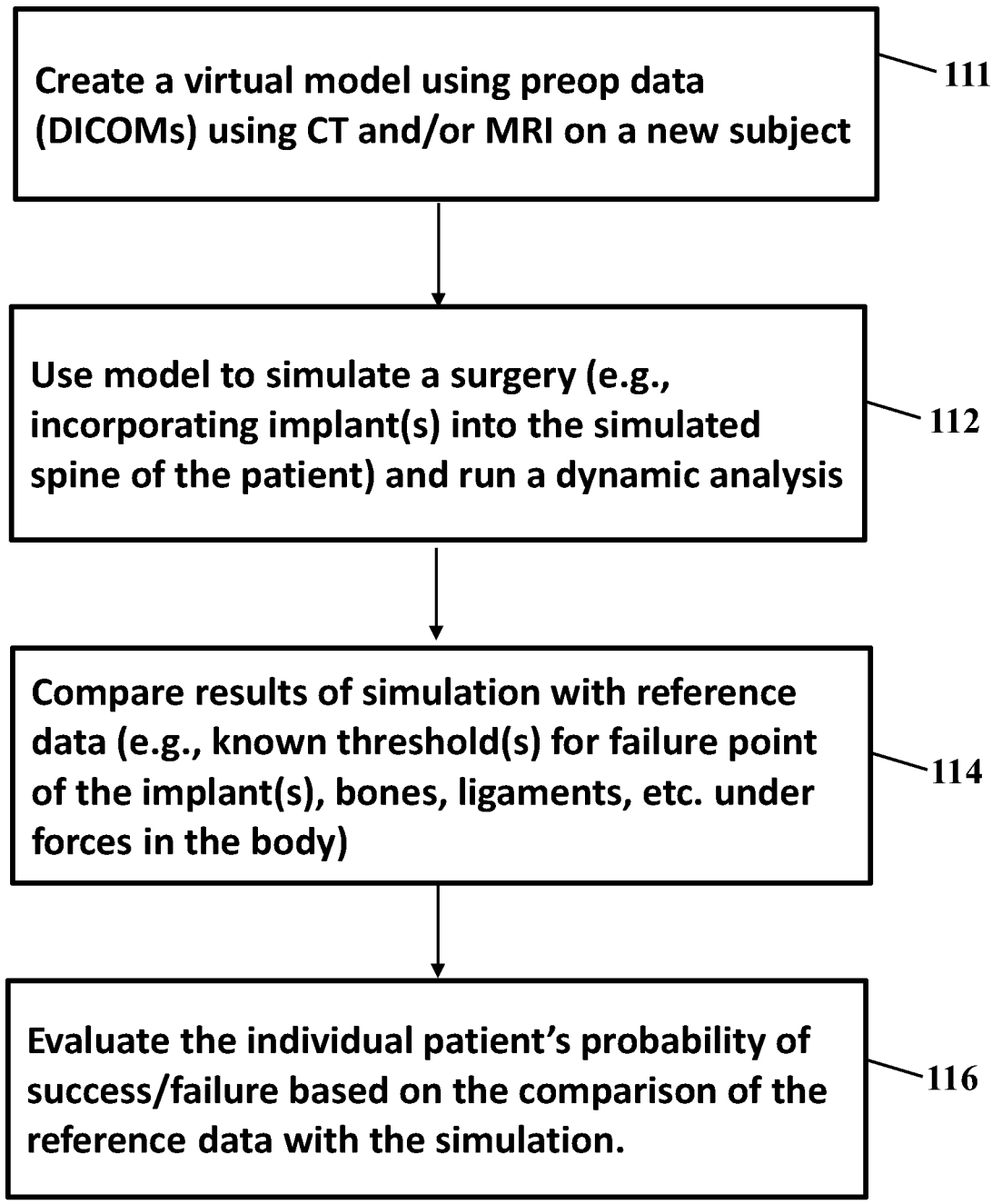
FIG. 11 list the steps taken in an exemplary implementation of the disclosed methods for a specific subject using reference data.

In the above paragraphs, with reference to FIGS. 5A and 5B example steps were provided in the implementation of the optimization module (FIG. 1, 101, FIG. 2, 201). In the example embodiment illustrated in FIGS. 5A and 5B, the trained and validated machine learning model from step 54A (in FIG. 5A) is used to establish the correlation between the model output and the patient's outcomes, i.e., which sets of parameters are associated with high success/failure outcomes (in FIG. 5B). In an alternative embodiment, as shown in FIG. 11, the machine learning model is not used and instead known or existing reference data and/or literature thresholds to predict the success/failure are used. For example, if a surgery is simulated by the incorporation of a titanium rod into the spine, a determination can be made that stresses on the titanium rod (due to the forces/moments applied on the rod) are exceeding the failure point of the titanium rod based on the known thresholds. In yet another embodiment, both the validated machine learning model from step 54A (in FIG. 5A) used to establish the correlation between the model output and the patient's outcomes and existing reference data and/or literature thresholds to predict the success/failure can be used.

With reference to FIG. 11, in step 111, a virtual model (e.g., a CAD model) is created on a new, current subject using their specific preop CT/MRI data (DICOMs). In step 112, this model is used to simulate a surgery for which the patient is under evaluation (for example, the simulated incorporation of a titanium rod or other implant(s) into a simulated spine of the patient) and dynamic analysis is run to simulate the patient's preoperative spine performance. In step 114, the results of the simulation including forces applied on the implant(s) are compared with reference data (such as, e.g., known threshold(s) for the failure point of the titanium rod or other implant(s), bones, ligaments, etc. under the forces in the body of the simulated patient). In step 116, a determination and/or evaluation can then be made with respect to the individual patient's probability for success or failure based on the comparison of the reference data with the simulation conducted in step 114. For example, in step 116, it can be determined whether stresses on the titanium rod or other implant(s) (due to the forces/moments applied on the rod or other implant(s)) are exceeding the failure point of the titanium rod or other implant(s) based on the known threshold(s), which would thus lead to a failure for a proposed implant(s) and/or surgical procedure for the individual patient.

Figure 12:
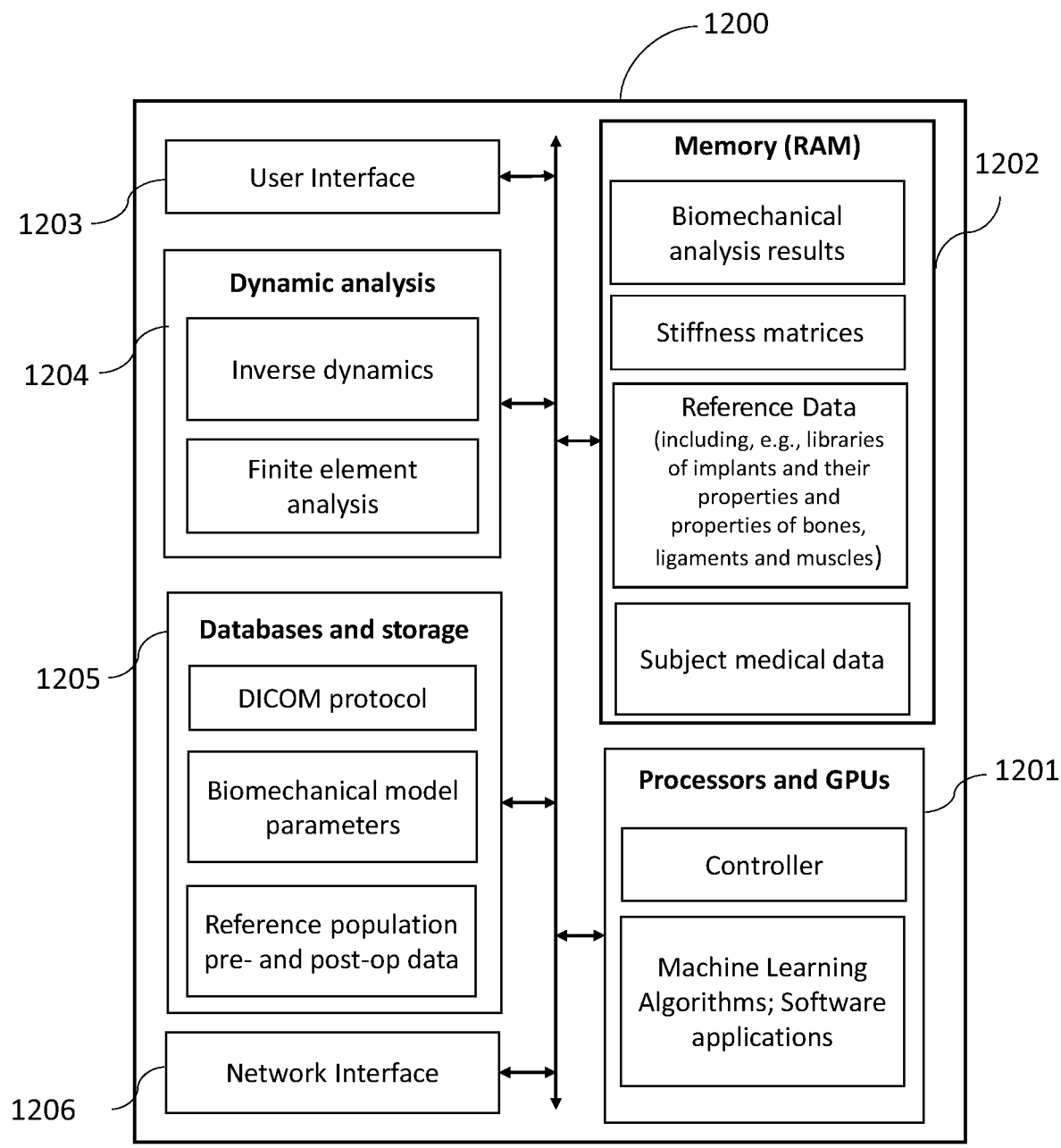
FIG. 12 illustrates another exemplary system used to implement the disclosed methods.

Reference is now made to FIG. 12, which shows a diagram of another illustrative system 1200 for implementing embodiments of the disclosed methods. The system 1200 comprises at least one processor and processor unit 1201, random access memory (RAM) 1202, a user interface 1203, a network interface 1206, a unit for dynamic analysis 1204, and at least one database or cloud storage 1205. The processor unit 1201 is configured to implement machine learning algorithms and/or software programs for comparing between results of a simulation and thresholds, as described in the above paragraphs, and a controller. The RAM 1202 includes the stiffness matrices (see, e.g., FIG. 9), reference data, including, e.g., libraries of implants (e.g., rods, etc.) having various characteristics and their properties suitable for various spinal levels and surgical indications, properties of bones, ligaments, and muscles, results of the biomechanical analyses, and subject medical data and imaging studies. The database or cloud storage 1205 comprises DICOM protocols, biomechanical model properties, and reference population pre-operative and post-operative data (see, e.g., FIG. 7). The dynamic analysis 1204 comprises the coding needed to perform the inverse dynamics and finite element analysis.

Figure 13:
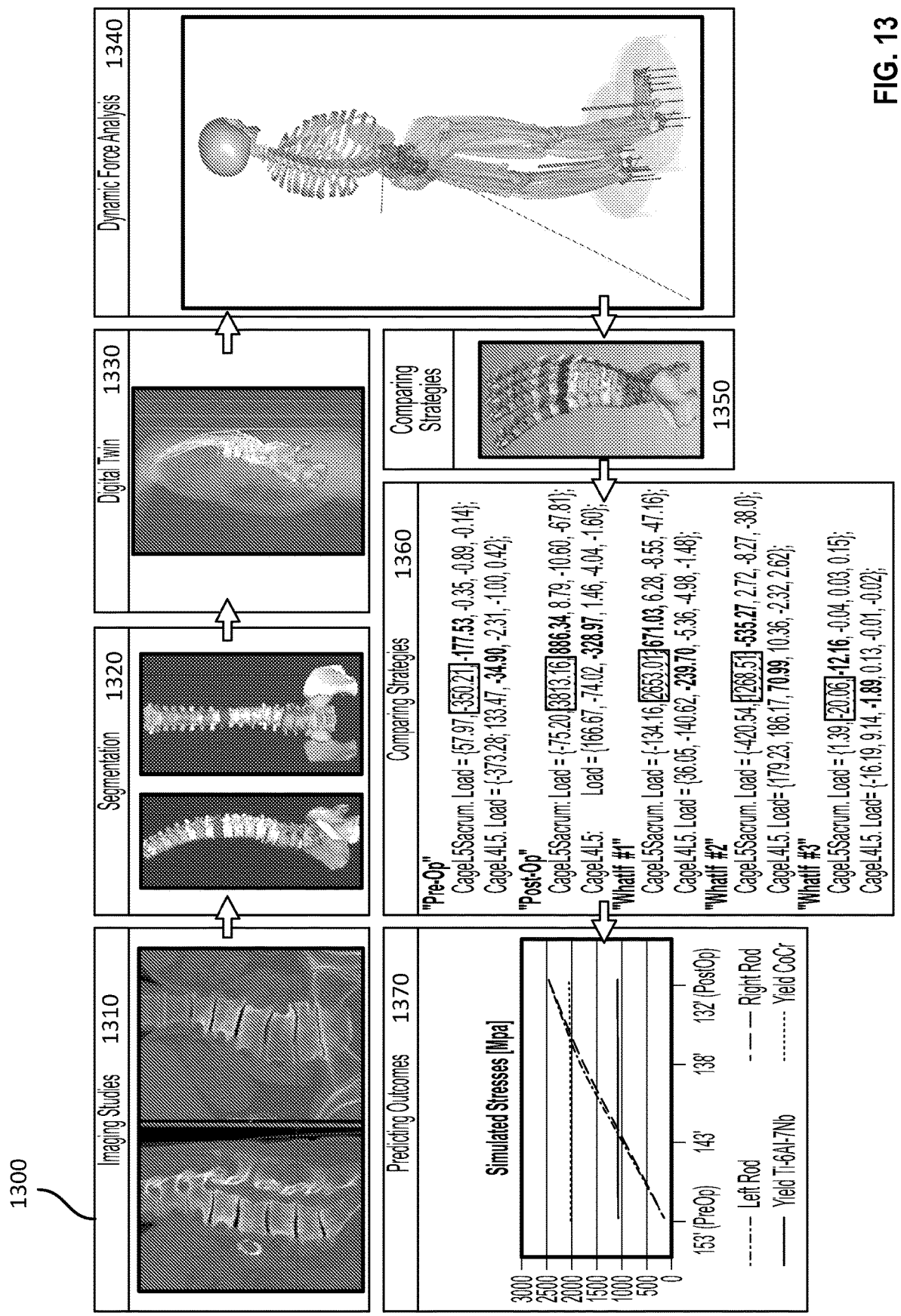
FIG. 13 details the steps in evaluating a specific subject in an exemplary implementation of the method.

FIG. 13 illustrates another module regarding a subject's individual analysis according to an embodiment of the invention. The module 1300 is based on three-dimensional anatomical modeling of the spine and soft tissues, which, in this embodiment, is derived from imaging studies 1310, automatic CT or MRI segmentation 1320 (with or without the use of convolution network architecture), and the creation of a digital twin 1330. The evaluation is performed on the upper body and analyzes elements such as: vertebrae, muscles, ligaments, discs and spinal range of motion; and anthropometric data. As discussed above, anthropometric measurements are a series of quantitative, systematic measurements of the size, shape and composition of the human body comprising measurements of the muscle, bone, and adipose tissue. Several core elements of anthropometry are height, weight, body mass index (BMI), body circumferences (waist, hip, and limbs), and skinfold thickness. These comprehensive anatomical and physiological data, including, e.g., the imaging studies 1310, segmentation 1320, and digital twin 1330, are used as the input to the dynamic force analysis module 1340.

The dynamic force analysis module 1340, virtual prediction and evaluation technology, can be based on at least one of, and typically both, musculoskeletal, finite element analysis, finite difference analysis, and finite volume analysis. The musculoskeletal model analysis, performed using, for example, AnyBody software, produces musculoskeletal models that simulate the human body working in concert with its environment. These simulations quantify forces, torques and motions inside the body, which are otherwise difficult to predict, measure, or determine. The goals of the biomechanical analyses comprise determining load-bearing requirements and optimizing implant positioning to improve the likelihood of surgical success. The finite element analysis, evaluates an implant(s) in the context of the subject's spine, and predicts reactions to real-world forces, moments, stresses, strains, and other physical effects. Finite element analysis is used to predict whether or how soon a given implant(s) will fail, or whether it will work in the way it was designed. These predictions may be based on, e.g., reference data, including, for example, the known materials properties for the material of which a specific implant is made, taking into account the stress acting on the spine-implant assembly. The output 1370 (e.g., predicting outcome(s)) of the subject analysis module 1300 comprises data on a set of potential implants, that includes comparing strategies 1350, 1360 of the set of potential implants that combine, e.g., the total forces, range of motion, and moments under various conditions, such as upright, spinal flexion and extension, right and left lateral bending, and right and left torsion. Such measurements are typically performed on each vertebral pair and joint, such as L1-L2, L2-L3, L3-L4, L4-L5, in the relevant region of the spine. The output 1370 of the biomechanical analysis for a given potential implant is provided in the context of its effect (e.g., simulated stresses) on both the joint into which it is to be implanted, e.g., L2-L3, as well as the predicted effect on the entire spinal region, e.g., L1-L5. As well, the output for each potential implant is compared to that for each implant in the set of implants being considered. By reviewing the output 1370 (e.g., simulated stresses), the various implants can be compared to determine whether stresses on certain implant(s) (due to the forces/moments applied on the implant(s)) are exceeding the failure point of the implant(s) based on, e.g., reference data, such as known threshold(s), which would thus lead to a failure for a proposed implant(s) and/or surgical procedure for the individual patient.

In the paragraphs, the methods and systems according to embodiments of the present disclosure are described by referring to the example of spine corrective surgery. However, as it must be appreciated, the above methods and systems are not limited to only spine corrective surgery but can be used in any orthopedic application or orthopedic surgery, for example, hip surgery, knee surgery, foot surgery, hand surgery, shoulder surgery, etc. The term "orthopedic" is used herein to refer to any musculoskeletal system including the spine, the arms, legs, joints and ligaments.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

We claim:

1. A method for predicting a success of a planned spinal surgical procedure, the method being implemented by a computer processor of a computer system, the method comprising:

receiving, at the computer system, pre-operative imaging data of a subject under evaluation for a spinal surgery;

receiving, at the computer system, at least one correlation between at least one of post-operative and pre-operative biomechanical parameters and a known outcome of a spinal surgical procedure for each one of at least some members of a reference population;

generating, by the computer processor using the pre-operative imaging data and at least one of anthropometric data of the subject, demographic data, or patient reported outcome measures (PROMs) a virtual three-dimensional (3D) biomechanical model of the spine of the subject under evaluation;

deriving, by the computer processor, pre-operative and post-operative biomechanical parameters from the virtual 3D biomechanical model of the spine of the subject to provide derived pre-operative and post-operative biomechanical parameters, wherein the deriving the pre-operative and post-operative biomechanical parameters is conducted by:

(i) segmenting, by the computer processor executing a machine learning algorithm comprising a convolutional neural network on the pre-operative imaging data, the spine of the subject in the generated virtual 3D biomechanical model of the spine of the subject, and applying, by the computer processor, inverse dynamics and finite element analysis to the segmented spine to provide at least the derived pre-operative biomechanical parameters; and (ii) simulating, by the computer processor, the planned spinal surgical procedure using the virtual 3D biomechanical model of the subject to provide at least the derived post-operative biomechanical parameters, wherein the simulating comprises:

sequentially inserting each of a plurality of potential virtual 3D implants into the 3D virtual biomechanical model, the plurality of potential virtual 3D implants corresponding to a plurality of potential physical 3D implants; and performing, for each potential virtual 3D implant in the plurality of potential virtual 3D implants, a dynamic analysis, resulting in the derived post-operative biomechanical parameters for each of the plurality of potential physical 3D implants;

applying, by the computer processor, to the derived pre-operative and post-operative biomechanical parameters of the subject the at least one correlation, thereby grading a predicted outcome of the planned spinal surgical procedure according to a predetermined rating with each of the plurality of potential virtual 3D implants to obtain a plurality of respective grades, resulting in a grading of the predicted outcome with each of the plurality of potential physical 3D implants; and selecting at least one of the plurality of potential physical 3D implants for use in the planned spinal procedure based on the grade of the at least one of the plurality of potential physical 3D implants.

2. The method according to claim 1, further comprising:

prior to receiving, at the computer system, the at least one correlation between the at least one of post-operative and pre-operative biomechanical parameters and the known outcome of the spinal surgical procedure for each one of at least some members of a reference population, analyzing, by the computer processor, at least one of post-operative and pre-operative imaging and/or at least one of post-operative and pre-operative anthropometric data of a member of the reference population, the member having undergone a spinal surgical procedure, to derive the at least one of post-operative and pre-operative biomechanical parameters of the member of the reference population;

grading, by the computer processor, the known outcome of the spinal surgical procedure according to a predetermined rating;

repeating, by the computer processor, the analyzing of the at least one of post-operative and pre-operative imaging and/or the at least one of post-operative and pre-operative anthropometric data and the grading of the known outcome of the spinal surgical procedure on additional members of the reference population; and determining, by the computer processor, the at least one correlation between the at least one of post-operative and pre-operative biomechanical parameters and the known outcome of the spinal surgical procedure for each one of the at least some of members of the reference population.

3. The method according to claim 1, wherein the spinal surgical procedure comprises one of a set of possible surgical interventions including artificial intervertebral disc replacement, spinal fusion, laminectomy, spinal deformity correction, and spinal decompression, and wherein the spinal surgical procedure comprises insertion of one or more hardware implants.

4. The method according to claim 1, wherein the predetermined rating comprises one of classifying success/failure, classifying at least three graded categories having success and failure as initial and final categories, a continuous scale determined using a linear regression analysis, or any combination thereof.

5. The method according to claim 1, wherein deriving at least one of the pre-operative and the post-operative biomechanical parameters comprises analyzing one or more of forces, moments, range of motion, stress analysis, ligament strength, and vertebral strength of at least some spinal segments.

6. The method according to claim 1, wherein deriving at least one of the pre-operative and the post-operative biomechanical parameters comprises determining a degree of deterioration of at least one of at least one vertebra, at least one intravertebral disc, at least one ligament, or at least one muscle.

7. The method according to claim 1, wherein at least one of the derived pre-operative and post-operative biomechanical parameters represent the spine of the subject at rest or in positions of motion.

8. The method according to claim 2, further comprising repeating, by the computer processor, the analyzing of the at least one of the post-operative and pre-operative imaging and/or the at least one of post-operative and pre-operative anthropometric data and the grading of the outcome of the spinal surgical procedure on additional members of the reference population until the at least one correlation reaches a predetermined level greater than a predetermined threshold.

9. The method according to claim 1, wherein the anthropometric data comprises one or more of body-mass index, body weight, height, and quantitative measurements of torso and limbs dimensions.

10. The method according to claim 1, wherein a success of the spinal surgical procedure is determined by at least one of patient reported outcome measures, radiological imaging results, functional outcome measures, or any combination thereof.

11. The method according to claim 1, wherein each of the derived biomechanical parameters has a range of values correlated with at least one of a successful outcome or an unsuccessful outcome, wherein the successful outcome refers to a specific spinal surgical procedure performed on a subset of members of the reference population.

12. The method according to claim 1, wherein the generated virtual 3D biomechanical model of the subject is used to assess a subject's current clinical orthopedic pathology and predict disease progression in absence of the planned spinal surgical procedure.

13. The method according to claim 1, wherein the predetermined rating is based on a composite score having a weighted sum of one or more of the derived biomechanical parameters.

14. The method according to claim 1, wherein the method is implemented by the computer processor using a machine learning algorithm.

15. The method according to claim 1, wherein the grading of the predicted outcome of the planned spinal surgical procedure enables a health practitioner to select at least one spinal surgical procedure from currently available spinal surgical procedures and implants.

16. The method according to claim 1, further comprising customizing at least one implant to the subject under evaluation for the spinal surgical procedure, wherein the at least one implant comprises an artificial intervertebral disc, or one or more of pedicle screws, spinal rods, and interbody spacers.

17. The method according to claim 1, wherein the pre-operative imaging data comprise at least one of three-dimensional CT, three-dimensional MRI images, or X-ray imaging in digital imaging and communications in medicine (DICOM) format, or any combination thereof.

18. The method according to claim 1, wherein the spinal surgical procedure is selected from the group consisting of an artificial intervertebral disc replacement, a spinal fusion, a laminectomy, a spinal decompression, and a procedure to correct an anatomical or physiological defect of the spine of the subject.

19. A method for predicting a success of a planned spinal surgical procedure, the method being implemented by a computer processor of a computer system, the method comprising:

a) analyzing biomechanical parameters derived from at least one of pre-operative imaging, pre-operative anthropometric data, post-operative imaging, and post-operative anthropometric data of a member of a reference population, the member having undergone a spinal surgical procedure;

b) grading the success of the spinal surgical procedure according to a predetermined rating;

c) repeating steps a) and b) on additional members of the reference population;

d) determining at least one correlation between post-operative and pre-operative biomechanical parameters and success of the spinal surgical procedure for each one of at least some of the members of the reference population;

e) for a subject under evaluation for a planned spinal surgical procedure, receiving pre-operative imaging data of the subject;

f) analyzing the pre-operative imaging data and at least one of anthropometric data, demographic data, or patient reported outcome measures (PROMs) to generate a virtual three-dimensional (3D) biomechanical model of the spine of the subject;

g) deriving pre-operative and post-operative biomechanical parameters from the virtual 3D biomechanical model of the spine of the subject to provide derived pre-operative and post-operative biomechanical parameters, wherein the deriving the pre-operative and post-operative biomechanical parameters is conducted by:

(i) segmenting the spine of the subject in the generated virtual biomechanical model of the spine of the subject by executing a convolutional neural network, and applying inverse dynamics and finite element analysis to the segmented spine to provide at least the derived pre-operative biomechanical parameters; and (ii) simulating the planned spinal surgical procedure using the generated virtual biomechanical model of the spine of the subject to provide at least the derived post-operative biomechanical parameters, wherein the simulating comprises:

sequentially inserting each of a plurality of potential virtual 3D implants into the 3D virtual biomechanical model, the plurality of potential virtual 3D implants corresponding to a plurality of potential 3D physical implants; and performing, for each potential 3D virtual implant in the plurality of potential virtual 3D implants, a dynamic analysis, resulting in the derived post-operative biomechanical parameters for each of the plurality of potential physical 3D implants;

h) applying to the derived pre-operative and post-operative biomechanical parameters of the subject, the at least one correlation determined in step d), to grade a predicted outcome of the planned spinal surgical procedure according to the predetermined rating with each of the plurality of potential physical 3D implants to obtain a plurality of respective grades, resulting in a grading of the predicted outcome with each of the plurality of potential physical 3D implants; and selecting at least one of the plurality of potential physical 3D implants for use in the planned spinal procedure based on the grade of the at least one of the plurality of potential physical 3D implants.

20. The method according to claim 19, further comprising:

generating, by the computer processor, a virtual biomechanical model for each one of the members of the reference population that had a spinal condition using at least one of pre-operative imaging data and anthropometric data corresponding to each one of the members of the reference population;

deriving, by the computer processor, at least one of pre-operative and post-operative biomechanical parameters of each one of the members of the reference population using the virtual 3D biomechanical model generated for each one of the members of the reference population; and determining, by the computer processor, using a trained machine learning algorithm, the at least one correlation between the at least one of post-operative and pre-operative biomechanical parameters and a success/failure of the spinal surgical procedure for each one of the members of the reference population.

21. A method comprising:

receiving, at a computer system, a plurality of pre-operative images of a patient preparing to undergo spine surgery;

generating, via at least one processor of the computer system based on the plurality of pre-operative images, a virtual three-dimensional (3D) biomechanical model of the spine of the patient;

receiving, at the computer system, an indication of a surgical operation of the spine which the patient may experience;

receiving, at the computer system, at least one correlation between at least one of post-operative and pre-operative biomechanical parameters and outcome of a spinal surgical procedure for each one of at least some members of a reference population;

deriving, by the computer processor, pre-operative and post-operative biomechanical parameters from the virtual 3D biomechanical model of the spine of the patient to provide derived pre-operative and post-operative biomechanical parameters, wherein the deriving the pre-operative and post-operative biomechanical parameters is conducted by:

(i) segmenting, by the at least one processor, by executing at least one machine learning algorithm on the plurality of pre-operative images, the spine of the subject in the virtual 3D biomechanical model of the spine of the subject, and applying inverse dynamics and finite element analysis to the segmented spine to provide at least the derived pre-operative biomechanical parameters; and (ii) simulating, via the at least one processor using the virtual 3D biomechanical model, the surgical operation of the spine of the patient, wherein the simulating comprises:

sequentially inserting each of a plurality of potential virtual 3D implants into the virtual 3D biomechanical model, the plurality of potential virtual 3D implants corresponding to a plurality of potential physical 3D implants; and performing, for each potential virtual 3D implant in the plurality of potential virtual 3D implants, a dynamic analysis, resulting in the derived post-operative biomechanical parameters for each of the plurality of potential physical 3D implants;

predicting, via execution of the at least one a-machine learning algorithm using the derived pre-operative and post-operative biomechanical parameters and the at least one correlation, a likelihood of success of the surgical operation of the spine for each of the plurality of potential physical 3D implants; and selecting at least one of the plurality of potential physical 3D implants for use in the surgical operation of the spine of the patient based on the likelihood of success of the selected at least one of the plurality of potential physical 3D implants.

22. The method of claim 21, wherein the at least one machine learning algorithm is trained by:

receiving, at the computer system, retrospective data of a plurality of patients having undergone an orthopedic surgical procedure, the retrospective data comprising: pre-operative training data and post-operative training data; and iteratively identifying correlations between the pre-operative training data and the post-operative training data to build a neural network, wherein the at least one machine learning algorithm comprises the neural network.

\* \* \* \* \*